United States Patent [19]

Chapman et al.

[11] Patent Number: 6,060,447
[45] Date of Patent: May 9, 2000

[54] PROTEIN COMPLEXES HAVING FACTOR VIII:C ACTIVITY AND PRODUCTION THEREOF

[75] Inventors: Barbara Chapman, Berkeley; Rae Lyn Burke, San Francisco, both of Calif.; Mirella Ezban Rasmussen, Copenhagen; Jan Moller Mikkelson, Gentofte, both of Denmark

[73] Assignees: Chiron Corporation, Emeryville, Calif.; Novo Nordisk A/S, Bagsvaerd, Denmark

[21] Appl. No.: 08/441,935

[22] Filed: May 16, 1995

Related U.S. Application Data

[62] Division of application No. 08/266,170, Jun. 27, 1994, Pat. No. 5,789,203, which is a continuation of application No. 07/652,099, Feb. 7, 1991, abandoned, which is a continuation-in-part of application No. 07/051,916, May 19, 1987, abandoned, which is a continuation-in-part of application No. 06/822,989, Jan. 27, 1996, abandoned.

[51] Int. Cl.[7] .................... G07K 14/255; A61K 38/37
[52] U.S. Cl. .............................. 514/12; 530/383
[58] Field of Search ................ 435/69.6, 172.3, 435/476; 530/383; 930/100; 514/2, 12

[56] References Cited

U.S. PATENT DOCUMENTS

| | | | |
|---|---|---|---|
| 4,657,894 | 4/1987 | Zimmerman et al. | 514/21 |
| 4,757,006 | 7/1988 | Toole et al. | 435/70 |
| 4,868,112 | 9/1989 | Toole, Jr. | 514/8 |
| 4,965,199 | 10/1990 | Capon et al. | 435/69.6 |
| 5,004,804 | 4/1991 | Kuo et al. | 530/387.9 |
| 5,045,455 | 9/1991 | Kuo et al. | 435/69.6 |
| 5,084,390 | 1/1992 | Hallewell | 435/188 |
| 5,149,637 | 9/1992 | Scandell et al. | 435/69.6 |
| 5,171,844 | 12/1992 | van Ooyen et al. | 530/383 |
| 5,198,349 | 3/1993 | Kaufman | 435/69.6 |

FOREIGN PATENT DOCUMENTS

| | | |
|---|---|---|
| 0210694 | 10/1984 | European Pat. Off. . |
| 0510735 | 8/1985 | European Pat. Off. . |
| 0160457 | 11/1985 | European Pat. Off. . |
| 082448 | 5/1986 | European Pat. Off. . |
| 0232112 | 8/1987 | European Pat. Off. . |
| 0251843 | 1/1988 | European Pat. Off. . |
| 0253455 | 1/1988 | European Pat. Off. . |
| 0254076 | 1/1988 | European Pat. Off. . |
| 0265778 | 5/1988 | European Pat. Off. . |
| 0534383 A2 | 3/1993 | European Pat. Off. . |
| WO 85/01961 | 5/1985 | WIPO . |
| WO 87/07144 | 12/1987 | WIPO . |
| WO 88/00831 | 2/1988 | WIPO . |
| WO 88/03558 | 5/1988 | WIPO . |
| WO 88/08035 | 10/1988 | WIPO . |
| WO 91/09122 | 6/1991 | WIPO . |
| WO 92/16557 | 10/1992 | WIPO . |

OTHER PUBLICATIONS

Burke et al. "The functional domains of coagulation factor VIII:C" (1986) *J. Biol. Chem.* 261:12574–12578.

Eaton et al. "Construction and Characterization of an active factor VIII variant lacking the central one–third of the molecule" (1986) *Biochemistry* 25:8343–8347.

Fulcher et al. "Human factor VIII procoagulant protein: Monoclonal antibodies define precursor–product relationships and functional epitopes" (1985) *J. Clin. Invest.* 76:117–124.

Gitschier et al. "Characterization of the human factor VIII gene" (1984) *Nature* 312:326–330.

Nordfang et al. "Generation of active coagulation factor VIII from isolated subunits" (1988) *J. Biol. Chem.* 263:1115–1118.

Orr et al. "'Spacer' function implied for the heavily glycosylated region of factor VIII" (1985) *J. Inter. Soc. Throm. Hemo.* 54:S321 (abstract).

Rotblat et al. "Purification of human factor VIII:C and its characterization by western blotting using monoclonal antibodies" (1985) *Biochemistry* 24:4294–4300.

Toole et al., "A large region (≈95 kDa) of human factor VIII is dispensable for in vitro procoagulant activity" (1986) *Proc. Natl. Acad. Sci. USA* 83:5939–5942.

Toole et al. "Molecular cloning of a cDNA encoding human antihaemophilic factor" (1984) *Nature* 312:342–347.

Truett et al. "Characterization of the polypeptide composition of human factor VIII:C and the nucleotide sequence and expression of the human kidney cDNA" (1985) *DNA* 4:333–349.

Vehar et al. "Structure of human factor VIII" (1984) *Nature* 312:337–342.

Wood et al. "Expression of active human factor VIII from recombinant DNA clones" (1984) *Nature* 312:330–337.

Yonemura et al. "Efficient production of recombinant human factor VIII by co–expression of the heavy and light chains" (1993) *Protein Engineering* vol. 6, No. 6, pp. 669–674.

*Primary Examiner*—Charles L. Patterson, Jr.
*Attorney, Agent, or Firm*—Roberta L. Robins; Joseph H. Guth; Robert P. Blackburn

[57] ABSTRACT

Recombinant protein complexes having human Factor VIII:C activity are expressed in a eukaryotic host cell by transforming the host cell with first and second expression cassettes encoding a first polypeptide substantially homologous to human Factor VIII:C A domain and a second polypeptide substantially homologous to human Factor VIII:C C domain, respectively. In the present invention, the first polypeptide may be extended having at its C-terminal a human Factor VIII:C B domain N-terminal peptide, a polypeptide spacer of 3–40 amino acids, and a human Factor VIII:C B domain C-terminal peptide. Expression of the second polypeptide is improved by employing an $\alpha_1$-antitrypsin signal sequence.

35 Claims, No Drawings

PROTEIN COMPLEXES HAVING FACTOR VIII:C ACTIVITY AND PRODUCTION THEREOF

CROSS-REFERENCE TO RELATED APPLICATION

This application is a divisional of U.S. patent application Ser. No. 08/266,170 filed Jun. 27, 1994 (now U.S. Pat. No. 5,789,203), which is a continuation of U.S. patent application Ser. No. 07/652,099 filed Feb. 7, 1991 (now abandoned), which is a continuation-in-part of U.S. patent application Ser. No. 07/051,916 filed May 19, 1987 (now abandoned), which is a continuation-in-part of U.S. patent application Ser. No. 06/822,989 filed Jan. 27, 1986 (now abandoned).

DESCRIPTION

1. Technical Field

This invention relates to protein complexes having Factor VIII:C activity, and to methods for producing said complexes by expression of suitable polynucleotide constructs. The protein complexes are useful in the treatment of classical (Type A) hemophilia.

2. Background of the Invention

Hemophilia A is an X-chromosome-linked inherited disease which afflicts 1–2 males per 10,000. The disease is caused by an absence or deficiency of Factor VIII:C. Factor VIII:C is a very large glycoprotein (native $M_r$ 330 K-360 K), which is present in plasma at extremely low concentrations. It is a necessary element in the proteolytic cascade which converts soluble fibrinogen to insoluble fibrin, forming a clot to prevent blood loss from traumatized tissue. In the bloodstream, it is found in noncovalent association with Factor VIII:R ("von Willebrand factor"), which acts as a stabilizing carrier protein. Factor VIII:C is very susceptible to cleavage by thrombin, plasmin, protease C, and other serine proteases. It is generally isolated from plasma or plasma products as a series of related polypeptides ranging from $M_r$ 160 K-40 K with predominant species of $M_r$ 92 K and $M_r$ 80 K-77 K. This complex pattern has made the analysis of the structure of active Factor VIII:C very difficult.

Factor VIII:C and the related polypeptides have been described by F. Rotblat et al, *Biochemistry* (1985) 24:4294–4300; G. A. Vehar et al, *Nature* (1984) 312:337–342; J. J. Toole et al, *Nature* (1984) 312:342–347; and M. A. Truett et al, *DNA* (1985) 4:333–349. E. Orr et al, *Molecular Genetics of Clotting Factors*, p. 54, s321, reported a "spacer" function for the heavily glycosylated region of Factor VIII:C. The sequence has been reported by J. J. Toole et al, supra; W. I. Wood et al, *Nature* (1984) 312:330–336; and M. A. Truett et al, supra. The full-length protein contains three repeats of one sequence (I), and two repeats of a second sequence (III). A third, heavily glycosylated sequence (II) is present between the second and third I repeats, and is apparently cleaved proteolytically to form the $M_r$ 92 K and $M_r$ 80 K polypeptides. The first two I repeats form the A domain, while the third I repeat and the two III repeats form the C domain. The II sequence forms the B domain. Thus, the full-length protein has the structure $I_1$-$I_2$-II-$I_3$-$III_1$-$III_2$ (A-B-C), while the $M_r$ 92 K and $M_r$ 80 X polypeptides (A and C) have the structures $I_1$-$I_2$ and $I_3$-$III_1$-$III_2$, respectively. C. Fulcher et al, *J Clin Invest* (1985) 76:117–124, suggested that based on antibody-epitope data with Factor VIII:C, both the $M_r$ 92 K and the $M_r$ 80 K polypeptides are necessary for Factor VIII:C function.

Factor VIII:C has historically been isolated from blood in a concentrated form for therapeutic treatment of hemophilia. However, concerns regarding transmission of HIV and other blood-borne diseases have stimulated activity to provide alternative supplies of Factor VIII:C. It is of substantial interest to be able to supply compositions having Factor VIII:C activity without concerns as to the transmission viral diseases associated with the native Factor VIII:C.

Although full-length recombinant human Factor VIII:C has been produced, it is difficult to purify and characterize, and it is unstable due to proteolysis. Efficient recombinant production of the full-length molecule for clinical use is doubtful at this time.

R. L. Burke et al, *J Biol Chem* (1986) 261:12574–78 disclosed the expression of an active Factor VIII:C complex from cells simultaneously transfected with polynucleotides encoding $M_r$ 92 K and $M_r$ 80 K polypeptides. The obtained protein demonstrated activity equal to that of cloned full-length Factor VIII:C expressed under similar conditions. O. Nordfang et al, *J Biol Chem* (1988) 263:1115–18 disclosed the in vitro assembly of active Factor VIII:C complexes from separate preparations of $M_r$ 92 K protein and $M_r$ 80 K protein (FVIII-HC and -LC, respectively). Successful assembly required divalent metal ions (especially $Mn^{++}$ and $Ca^{++}$) and thiols, but only a small amount of FVIII-HC could be complexed into active FVIII:C.

DISCLOSURE OF THE INVENTION

We have now invented an improved method for expressing recombinant protein complexes with high stability and Factor VIII:C activity. The $M_r$ 92 K polypeptide (FVIII-HC) and the $M_r$ 80 K polypeptide (FVIII-LC) are expressed as two separate polypeptides, under the control of separate promoters, within the same host cell. Each polypeptide is preferably expressed using a signal sequence which directs export to the extracellular space with cleavage of the signal sequence. FVIII-HC is preferably expressed as a fusion protein having a C-terminal extension. The extension comprises a polypeptide sequence homologous to the B domain N-terminal sequence (which may allow cleavage by thrombin), a polypeptide spacer of 3 to 100 amino acids, and a sequence homologous to the C-terminal B domain sequence. The C-terminal extension of FVIII-HC results in a higher yield of active polypeptide upon expression in eukaryotic host cells. FVIII-LC is preferably expressed as an LC polypeptide using a signal peptide. The FVIII-LC polypeptide is processed and secreted efficiently with the correct N-terminal amino acid residue, and correct glycosylation. Cotransfection with polynucleotides encoding FVIII-HC and FVIII-LC in a suitable host cell provides recombinant protein complexes having Factor VIII:C activity in high yield.

MODES OF CARRYING OUT THE INVENTION

A. Definitions

The term "polynucleotide" as used herein refers to a sequence of DNA or RNA, which may be single or double-stranded (ss or ds), or a DNA-RNA heteroduplex. In most cases herein, polynucleotide will refer to dsDNA.

The term "signal peptide" as used herein refers to a peptide sequence which is recognized and acted upon by signal peptidase during expression of the polypeptide. Signal peptides encode peptide sites for signal peptidase cleavage, and cause the attached polypeptide to be transported into the secretion pathway leading to the extracellular medium.

The term "A domain" refers to that portion of human Factor VIII:C which constitutes the $M_r$ 92 K protein subunit.

The A domain contains from about 740 to about 760 amino acids and is found at the N-terminus of the native human Factor VIII:C. The A domain polypeptide will extend from amino acid 10, usually amino acid 1, to at least about amino acid 620, usually at least about amino acid 675, more usually at least about amino acid 740. The polypeptide will include at least about 85% of the A domain (Wood et al, supra), more usually at least about 90% and may optionally include a portion of the N-terminus of the B domain, typically not exceeding about amino acid 1405. Of particular interest is an N-terminal chain having the entire sequence to the thrombolytic cleavage site at $Arg_{740}$-$Ser_{741}$.

The term "B domain" refers to that portion of native human Factor VIII:C which is generally removed by intracellular cleavage, and which is heavily glycosylated when expressed in mammalian cells such as COS7 and CHO. The B domain contains an N-terminal sequence, which allows cleavage of the A domain from the B domain by thrombin. The B domain also has a C-terminal processing site which allows cleavage of the C domain from the A-B precursor by an enzyme located in the Golgi apparatus of the mammalian cell. The sequences of the N-terminal and C-terminal sequences are set forth in the Examples below. The complexes of the invention which lack "a substantial portion of the B domain" lack all of the B domain, or essentially all of the B domain except for the N-terminal and C-terminal sequences.

The term "C domain" refers to that portion of native human Factor VIII:C which constitutes the C-terminus of the full length protein, and is cleaved intracellularly to form the Factor VIII:C light chain. The light chain will have an amino acid sequence substantially the same as the amino acid sequence of the C-terminus of a Factor VIII:C polypeptide, usually at least about 80%, more usually at least about 90% of the Factor VIII:C $M_r$ 80 K chain, particularly beginning with amino acid 1570, usually amino acid 1600, particularly amino acid 1625, more particularly amino acid 1640, preferably at about amino acid 1649, ±10 amino acids, more particularly ±1 amino acid, and continuing to at least about amino acid 2300, usually 2310, ±10 amino acids, preferably 2325, ±5 amino acids, more preferably to the terminal amino acid (2332). Usually, the light chain will have at least about 85%, more usually at least 95%, of the C1-C2 domains, desirably the A3-C1-C2 domains.

The term "co-expressing" as used herein refers to simultaneous expression of an A domain polypeptide and a C domain polypeptide within the same host cell. The polynucleotide sequences encoding the A and C domains may be on the same or on different expression cassettes or plasmids. Co-expression of the A and C domains permits proper folding to occur, which in turn provides an A-C complex having higher activity and efficiency of secretion.

The term "cell growth medium" as used herein refers to any medium suitable for culturing host cells, and includes media suitable for obtaining expression of recombinant products whether actual cell "growth" occurs or not. Cell growth media generally include nutrients and a metabolizable energy source in an aqueous solution. If desired, cell growth media may also include a compound which induces expression of the recombinant polypeptides of the invention. Selection of such an inducing compound depends upon the promoter selected to control expression. Other typical additives include selection compounds (i.e., drugs or other chemicals added to the media to insure that only transformed host cells survive in the medium) and serum, such as fetal bovine serum (FBS). "Serum-free medium" is a solution which has been supplemented to such an extent that the necessary trace factors present in serum need not be added in the form of serum. There are many suitable cell growth media available from commercial sources.

The term "polypeptide spacer" refers to a polypeptide sequence of about 3 to about 100 amino acids, which is generally not homologous to the human Factor VIII:C B domain, and which carries fewer than 5 potential sites of N-linked glycosylation. Preferably, there will be 2 or fewer such sites. It is presently believed that the large size and high degree of glycosylation of the B domain prevents efficient expression of the $M_r$ 92 K polypeptide. However, a low (but useful) yield of the $M_r$ 92 K polypeptide is obtained when the B domain is completely removed. It is also presently believed that the A domain may not be folded correctly on a consistent basis in the absence of the B domain, so that only a small percentage of the A domain is correctly folded and expressed. The polypeptide spacer of the invention provides a C-terminal extension to the A domain, and apparently stabilizes the polypeptide and improves secretion in active form. Thus, it may be that use of a polypeptide which is glycosylated lightly (or not at all) prevents the A domain-spacer construct from encountering the same size problems obstructing expression of full-length Factor VIII:C. The presently preferred spacer is derived from a human Ig heavy chain hinge, particularly from human IgAl. This spacer provides a flexible extension, without adding an immunogenic epitope (when administered in humans).

The term "homology" as used herein means identity or substantial similarity between two polynucleotides or two polypeptides. Homology is determined on the basis of the nucleotide or amino acid sequence of the polynucleotide or polypeptide. In general terms, usually not more than 10, more usually not more than 5 number %, preferably not more than about 1 number % of the amino acids in the chains will differ from the amino acids naturally present in the Factor VIII:C A and C domains. Particularly, not more than about 5%, more usually not more than about 1% will be nonconservative substitutions. Conservative substitutions include:

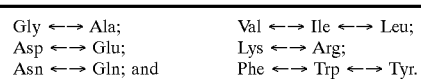

| Gly ←→ Ala; | Val ←→ Ile ←→ Leu; |
| Asp ←→ Glu; | Lys ←→ Arg; |
| Asn ←→ Gln; and | Phe ←→ Trp ←→ Tyr. |

Nonconservative changes are generally substitutions of one of the above amino acids with an amino acid from a different group (e.g., substituting Asn for Glu), or substituting Cys, Met, His, or Pro for any of the above amino acids.

The term "sufficient amount" of protein complex of the invention refers to that amount of protein which is capable of effecting therapeutic treatment of a subject having a disorder treatable with native human Factor VIII:C. In general, the protein complex of the invention is essentially as active as native human Factor VIII:C, and may be administered in similar amounts. The specific activity of the protein complex of the invention may be determined by means known in the art, as described below (e.g., by using the commercially available COATEST assay).

The term "effective concentration" refers to a concentration of expression cassette which is capable of transforming a host cell under appropriate transformation conditions.

B. General Method

DNA constructs are generally employed for expression of the polypeptides of the invention. Each of the polynucleotide constructs will have, in the 5'-3'-direction of transcription, a transcriptional initiation and translational initiation region, a structural gene coding region comprising a sequence coding for the signal peptide sequence, and a sequence coding for the Factor VIII:C heavy or light chains, followed by translational and transcriptional termination sequences. The selection of specific elements such as these is within the skill of the art.

The initiation region may comprise a number of different sequences related to the initiation of transcription and translation. These sequences include enhancer sequences, RNA polymerase binding site, RNA capping site, ribosomal binding and translational initiation sites, and the like. The transcriptional initiation region may be the natural region associated with Factor VIII:C, or may be an alternative sequence to provide for higher transcriptional efficiency. The sequences may be obtained from mammalian viruses or the genes of the host cell or genes from a different mammalian host which are active in the host cell. Numerous transcriptional initiation regions have been isolated and demonstrated to be operative in mammalian host cells. These regions include the SV40 early promoter and late promoter regions, the adenovirus major late promoter region, actin promoter region, the cytomegalovirus $M_r$ 72 K immediate early protein promoter region, the metallothionein promoter, and the like.

The termination region may include 3'-untranslated sequences, a polyadenylation signal sequence, and the like. The termination region may be obtained from the 3' non-translated sequence of the Factor VIII:C natural cDNA, or may be from the same structural gene or different structural gene from which the 5'-initiation region was obtained. The 3'-region is not as essential to the level of transcription as the initiation region, so that its choice is more of a matter of convenience than specific selection.

The structural genes typically include a leader sequence coding for the signal peptide which directs the polypeptide into the lumen of the endoplasmic reticulum for processing and maturation. Optionally included are additional sequences encoding propeptides which are processed post-translationally by endopeptidases, where the endopeptidases cleave a peptide bond, removing the propeptide to generate the mature polypeptide. The signal peptide may be the naturally occurring one, particularly for the N-terminal peptide, or may be any signal peptide which provides for the processing and maturation of the polypeptides.

Various signal peptides have been reported in the literature and include such sequences as that of tissue plasminogen activator, immunoglobulin heavy and light chains, viral membrane glycoproteins such as Herpes Simplex virus glycoproteins gB and gD, $\alpha_1$-antitrypsin, and the like. The $\alpha_1$-antitrypsin signal peptide is presently preferred for secretion of the FVIII-LC polypeptide.

The DNA sequences encoding the mature protein and signal peptide must be joined so as to be in reading frame. Where convenient restriction sites are available, the cohesive or blunt ends may be properly joined. However, for the most part, adapters will be employed where portions of the coding sequence will be recreated in the synthetic adaptor so that the truncated structural gene and/or truncated signal sequence will be linked through the adaptor, so as to be in proper reading frame. The signal sequence and structural gene may be partially restriction mapped, so as to identify restriction sites, particularly unique restriction sites, which may be employed to link the two sequences together in proper reading frame by means of an appropriate adaptor. Alternatively unique restriction sites may be inserted at the junction of the signal sequence and mature polypeptide coding sequence by in vitro mutagenesis.

The translational start and stop signals will normally be part of the structural gene, providing for the initiation codon at the beginning of translation and one or more stop codons for the termination of translation. The initiation codons will be the first codons of the signal sequences. The stop codons may be added as appropriate as part of the termination region or be added to the coding region to provide for convenient 3'-terminus for linkage to the transcriptional termination region to provide for a complete termination region.

The various regions of the expression cassette, (the transcriptional and translational initiation region nucleic acid sequence, structural gene nucleic acid sequence encoding one of the polypeptides and under the transcriptional and translational control of the initiation region, and a transcriptional and translational termination region, controlling the processing of the mRNA and the translational termination) which identify the particular nucleotide sequences may be joined using conventional methods. Usually, the sequences obtained will contain, or be modified to contain restriction sites, which may then be annealed where complementary overhangs or cohesive ends are present. Modification frequently will be in noncoding regions by the introduction of linkers to provide for the desired cohesive ends. The ends will usually be ligated prior to introduction into the host cell, although the host cell may be allowed to provide the necessary ligation.

The expression cassettes may be joined to a wide variety of other sequences for particular purposes. Where amplification of the amount of secreted glycoprotein is desired, the expression cassettes for FVIII:C may be joined in tandem to a gene for which spontaneous increases in gene copy number can be selected by an appropriate treatment. Such genes include the human metallothionein gene, and the mouse dihydrofolate reductase gene. These genes are placed in cassettes having their own transcriptional and translational regulatory sequences. By selecting cell clones resistant to increasing concentrations of heavy metal ions (e.g., cadmium) or methotrexate, the gene of interest (the expression cassette) may be co-amplified in the host cell.

The subject expression cassettes may be part of a vector comprising a replication system functional in the host cell, which replication system may provide for stable episomal maintenance or integration of the expression cassette into the host genome. The vector will also comprise a marker for selection, for selecting mammalian host cells containing the DNA construct and the vector from those host cells which lack the DNA construct and vector.

A wide variety of replication systems are available, typically derived from viruses that infect mammalian host cells. Illustrative replication systems include the replication systems from Simian virus 40, adenovirus, bovine papilloma virus, polyoma virus, Epstein Barr virus, and the like.

Selection markers enabling propagation of the vector in prokaryotic host cells may include resistance to a biocide, particularly an antibiotic, or complementation of auxotrophy to provide a prototrophic host. Particular genes of interest as markers include kanamycin resistance gene (NPTII), chloramphenicol resistance gene (CAT), penicillinase (p-lactamase), or the like.

The vector will usually be circular, and will have one or more restriction sites which allow for the insertion of the expression cassette, stepwise or as a completed entity, into the vector. Frequently, the vector will also include a bacterial replication and selection system, which allows for cloning after each of the manipulative steps. In this way, relatively large amounts of the construction at each of the stages may be prepared, isolated, purified, tested to verify that the proper joining has occurred, and then used for the next stage.

Various mammalian host cells may be employed in which the regulatory sequences and replication system are functional. Such cells include COS7 cells, Chinese hamster ovary (CHO) cells, mouse kidney cells, hamster kidney cells, HeLa cells, HepG2 cells, or the like.

The expression cassettes of the desired polypeptides may be linked together in one nucleic acid chain or may be provided in separate nucleic acid molecules. The expression cassettes may be parts of different vectors or of the same vector. This is primarily a matter of convenience, although in some situations with particular vectors, one or the other manner of construction may be preferable.

The expression vector may be a replication-deficient retrovirus. S.-F. Yu et al, *Proc Nat Acad Sci USA* (1986) 83:3194–98 disclosed the construction of self-inactivating ("SIN") retroviral gene transfer vectors. SIN vectors are created by deleting the promoter and enhancer sequences from the U3 region of the 3' LTR. A functional U3 region in the 5' LTR permits expression of the recombinant viral genome in appropriate packaging cell lines. However, upon expression of its genomic RNA and reverse transcription into cDNA, the U3 region of the 5' LTR of the original provirus is deleted, and is replaced with the U3 region of the 3' LTR. Thus, when the SIN vector integrates, the non-functional 3' LTR U3 region replaces the functional 5' LTR U3 region, and renders the virus incapable of expressing the full-length genomic transcript.

The expression cassettes are introduced into the host cell by conventional methods. Conveniently, calcium phosphate-precipitated DNA or DNA in the presence of DEAE-dextran may be employed for transformation. A synthetic lipid particularly useful for polynucleotide transfection is N-[1-(2,3-dioleyloxy)propyl]-N,N,N-trimethylammonium chloride, which is commercially available under the name Lipofectin® (available from BRL, Gaithersburg, Md.), and is described by P. L. Felgner et al, *Proc Nat Acad Sci USA* (1987) 84:7413. Where viruses are involved, transfection or transduction may be employed. The particular manner in which the host cell is transformed is not critical to this invention, depending substantially upon whether the expression cassettes are joined to a replication system and the nature of the replication system and associated genes.

The transformed/transfected cells are then grown in an appropriate nutrient medium. It is presently preferred to employ CHO cells cultured at 10 to 32° C., more preferably about 27° C., for less than about 30 hours, more preferably less than 10, most preferably less than about 4 hours. The product is obtained as a complex of the two FVIII:C chains, so that the media or cell lysate may be isolated and the Factor VIII:C active complex extracted and purified. Various means are available for extraction and purification, such as affinity chromatography, ion exchange chromatography, hydrophobic chromatography, electrophoresis, solvent-solvent extraction, selective precipitation, and the like. The particular manner in which the product is isolated is not critical to this invention, and is selected to minimize denaturation or inactivation and maximize the isolation of a high-purity active product.

Compositions are provided where the composition in the COATEST assay will have at least 0.02 U/mL of activity, usually at least about 0.2, more usually at least about 0.5 U/mL of activity. The subject product can be purified by affinity chromatography using antibodies, particularly monoclonal antibodies directed against the FVIII-LC, electrophoresis, extraction, HPLC, etc.

The subject method provides for production of a complex of the heavy and light chains which has Factor VIII:C activity. Production is evidenced by conditioned media as described in the experimental section, which will have at least about 50, usually at least about 70 mU/mL, more usually at least about 200 mU/mL of Factor VIII:C activity in the COATEST assay.

The complexes having Factor VIII:C activity produced according to the invention have a variety of uses as immunogens for the production of antibodies, for isolation of von Willebrand factor by affinity chromatography, in diagnostic assays for Factor VIII:C and for treatment of hemophiliacs and other hosts having blood clotting disorders. The subject protein complexes may be administered in a physiologically acceptable carrier, such as water, saline, phosphate buffered saline, and citrate buffered saline, at concentrations in the range of about 10–200 U/mL. See U.S. Pat. Nos. 3,631,018; 3,652,530, and 4,069,216 for methods of administration and amounts. Other conventional additives may also be included.

C. EXAMPLES

The examples presented below are provided as a further guide to the practitioner of ordinary skill in the art, and are not to be construed as limiting the invention in any way.

Example 1

Preparation of Expression Plasmids (A) pSV7d

The expression cassettes were prepared using the mammalian cell expression vector pSV7d (2423 bp).

The plasmid pSV7d (see Truett et al, supra) was constructed as follows: The 400 bp BamHI/HindIII fragment containing the SV40 origin of replication and early promoter was excised from pSVgtI (obtained from Paul Berg, Stanford University, California) and purified. The 240 bp SV40 BclI/BamHI fragment containing the SV40 polyA addition site was excised from pSV2/DHFR (Subramani et al, *Mol Cell Biol* (1981) 1:854–864) and purified. The fragments were fused through the following linker:

```
                              Stop Codons 1   2   3

5'-AGCTAGATCTCCCGGGTCTAGATAAGTAAT-3'  (SEQ ID NO:1)
                |        TCTAGAGGGCCCAGATCTATTCATTACTAG (SEQ ID NO:2)
                |    |    |    |
          HindIII BglII SmaI XbaI        BclI overhang.
```

This linker contains five restriction sites, as well as stop codons in all three reading frames. The resulting 670 bp fragment containing the SV40 origin of replication, the SV40 early promoter, the polylinker with &top codons and the SV40 polyadenylation site was cloned into the BamHI site of pML, a pBR322 derivative having about 1.5 Kb deleted (Lusky and Botchan, Cell (1984) 36:391), to yield pSV6. The EcoRI and EcoRV sites in the pML sequences of pSV6 were eliminated by digestion with EcoRI and EcoRV, treated with Bal31 nuclease to remove about 200 bp on each end, and finally religated to yield pSV7a. The Bal31 resection also eliminated one BamHI restriction site flanking the SV40 region, approximately 200 bp away from the EcoRV site. To eliminate the second BamHI site flanking the SV40 region, pSV7a was digested with NruI, which cuts in the pML sequence upstream from the origin of replication. This was recircularized by blunt end ligation to yield pSV7b.

pSV7c and pSV7d represent successive polylinker replacements. First, pSV7b was digested with StuI and XbaI. Then, the following linker was ligated into the vector to yield pSV7c:

```
BglII  EcoRI SmaI  KpnI  XbaI
  |      |    |     |     |
5'-AGATCTCGAATTCCCCGGGGTACCT (SEQ ID NO:3)
   TCTAGAGCTTAAGGGGCCCCCATGGAGATC (SEQ ID NO:4)
```

Thereafter, pSV7c was digested with BglII and XbaI, and then ligated with the following linker to yield pSV7d:

```
BglII   EcoRI SmaI  XbaI  BamHI SalI
  |       |    |     |      |    |
5'-GATCTCGAATTCCCCGGGTCTAGAGGATCCGTCGAC (SEQ ID NO:5)
       AGCTTAAGGGGCCCAGATCTCCTAGGCACGTGGATC (SEQ ID NO:6)
```

(B) pSVF8-92 pSVF8-92 is an expression plasmid for the $M_r$ 92 K FVIII-HC chain. Starting from the BamHI site in the polylinker pSV7d, pSVF8-92 consists of a 49 bp synthetic linker-adaptor molecule from BamHI to SacI encoding nucleotides −30 to +14 of the Factor VIII:C cDNA, (numbering from the first A of the translational start site; the sequence is shown below in (D) a 2267 bp SacI to HindIII fragment from the Factor VIII:C DNA contained in pSVF8-200 described below (up to nucleotide +2281), and pSV7d from HindIII to BamHI.

(C) DSVF8-80 pSVF8-80 is an expression plasmid for the $M_r$ 80 K FVIII-LC chain. Starting from the SalI site in the polylinker pSV7d, pSVF8-80 consists of a 201 bp fragment of a tissue plasminogen activator cDNA from nucleotides −98 to +103 (relative to the start codon) terminating at a BglII site (tPA sequences given in S. J. F. Degan et al, *J Biol Chem* (1986) 261:6972–6985), a 29 bp synthetic BglII to BclI linker-adaptor encoding nucleotides +5002 to +5031 of Factor VIII:C ligated to a 2464 bp BclI fragment of factor VIII:C spanning from a BclI site created at nucleotide 5028 of the factor VIII:C cDNA through in vitro mutagenesis (Zoller and Smith, *Meth Enzymol* (1983) 100:468) (pF8GM7), to a BclI site in the 3' untranslated region, at nucleotide 7492, and a 400 bp fragment of tPA 3' untranslated sequence spanning from a BglII site to a synthetic PstI site generated from the cDNA cloning, followed by the polylinker from the vector M13mp9 (Vieira and Messing, *Gene* (1982) 19:259) and then pSV7d.

(D) pSVF8-200

The vector pSVF8-200 is an expression plasmid for the full-length Factor VIII:C cDNA. The plasmid pSVF8-200 (described in Truett et al), which contains the entire Factor VIII:C cDNA coding and 3' untranslated sequences, with the 5' untranslated sequences the same as described above for pSVF8-92, was prepared as follows.

Plasmid pSV7d was digested with BamHI to cut in the polylinker region downstream of the SV40 early promoter. The following 49 bp BamHI-SacI linker adaptor, which codes for the last 30 bp of the 5' untranslated region and the first 15 bp of the human Factor VIII:C coding sequence, was chemically synthesized and ligated to pSV7d.

```
       -35    -30    -25    -20    -15    -10    -5
5'       GATCC TCTCC AGTTG AACAT TTGTA GCAAT AAGTC

3'   BamHI G AGAGG TCAAC TTGTA AACAT CGTTA TTCAG

Met Gln Ile Glu

ATG CAA ATA GAG CT      3'  (SEQ ID NOS:7-8)

TAC GTT TAT CSacI       5'  (SEQ ID NO:9)
```

This ligated plasmid was subsequently digested with SacI to remove excess linkers and with SalI to provide a SalI overhang.

Fragment 1, the 2.9 K SalI fragment from pF8-102 containing the 5' coding region of human Factor VIII:C, and Fragment 2, the 6.5 K SacI-SalI fragment from pF8-6.5 which contains the 3' coding region of the factor, and pSV7d modified vector containing the linker adaptor were ligated together (see Truett et al, supra). This ligation mix was then used to transform *E. coli* HB101, and colonies were selected by resistance to ampicillin.

Three hundred transformants were screened by colony filter hybridization using the BamHI-SacI 5' adaptor or the 2.9 K SacI fragment as probes. Those colonies positive with both probes were then analyzed by restriction mapping. Plasmid pSVF8-200, which contains the entire coding region for the human Factor VIII:C gene and a 5' untranslated region properly fused in transcriptional orientation to the SV40 early promoter, was obtained.

(E) Transfection and Culture of COS7 Cells

The plasmids described above were transfected into COS7 cells (Guzman, *Cell* (1981) 23:175) using the calcium phosphate coprecipitation method (van der Eb and Graham, *Meth Enzymol* (1980) 65:826–39) coupled with treatment with chloroquine diphosphate (Luthman and Magnusson, *Nuc Acids Res* (1983) 11:1295–1308) using 50 µg of plasmid DNA per $5 \times 10^5$ cells for 14 hr. Cells may also be transfected by the DEAE-dextran method of Sompayrac and Danna, *Proc Nat Acad Sci USA* (1981) 78:7575–78.

The COS7 cells were cultured in Dulbecco's modified Eagle medium supplemented with 10% fetal calf serum, 100 U/mL penicillin, 100 µg/mL streptomycin, 292 µg/mL glutamine, and 110 µg/mL sodium pyruvate. Samples were obtained from a 48-hour collection of serum-containing medium at 88 hours post transfection.

(F) Assays

At specific intervals post transfection, medium was removed from the cells, and aliquots were stored at −70° C.

Samples were tested for their ability to decrease the prolonged partial thromboplastin time of Factor VIII:C deficient plasma in a standard coagulation assay (Hardisty et al, *Thromb et Diathesis Haemolog* (1962) 72:215). The more specific COATEST assay (Rosen et al, *Thromb and Haemostasis* (1985) 54:818–823), which measures the generation of activated Factor X (Xa) as a linear function of the concentration of exogenously supplied Factor VIII:C, was used to verify the results of the coagulation assay. The concentration of immunologically reactive Factor VIII:C protein in the medium was determined by the application of a radioimmunoassay (RIA) developed to detect the $M_r$ 92 K polypeptide and by an enzyme-linked immunosorbant assay (ELISA) specific for the $M_r$ 80 K polypeptide (Nordfang et al, *Thromb Haemostasis* (1985) 53:346).

As shown in Table 1, expression of the $M_r$ 92 K polypeptide or of the $M_r$ 80 K polypeptide alone produced no detectable activity even though high levels of each of the individual proteins were present in the conditioned media. When cells were cotransfected with pSVF8-92 and pSVF8-80 plasmids, the media contained about 20 mU/mL of coagulation activity. The same relative level of the coagulation activity was secreted by cells transfected with the plasmid pSVF8-200 encoding the complete Factor VIII:C protein.

When conditioned media from the pSVF8-92 and the pSVF8-80 single transfectants were mixed together (using several different conditions as outlined in Table 1) no activity was measurable.

These results indicate that a complex of the amino and carboxyl terminal domains of Factor VIII:C retains intrinsic coagulation activity and that the interior domain is not essential for activity nor for the assembly of an active complex from separate chains.

TABLE 1

Assay of Recombinant Factor VIII:C Activity in Conditioned COS7 Cell Media

| Plasmid | Coagulation Time (sec) | Coagulation Activity mU/mL | COATEST Activity mU/mL | HC-RIA Assay U/mL | LC-ELISA Assay U/mL |
|---|---|---|---|---|---|
| pSVF8-92 | 95.7 | <0.9 | <0.1 | 0.15 | <0.0002 |
| pSVF8-80 | 97.2 | <0.9 | <0.1 | <0.01 | 1.36 |
| PSVF8-92 & pSVF8-80[a] | 56.1 | 22.5 | 20.4 | 0.05 | 1.13 |
| pSVF8-200 | 47.7 | 70.0 | 43.2 | 0.12 | 0.28 |
| none | 94.6 | <0.9 | <0.1 | <0.0 | <0.0002 |
| pSVF8-92J + pSVF8-80[b†] | 95.7 | <0.9 | <0.1 | — | — |

[a] plasmids were cotransfected into the same cells
[b] plasmids were transfected into separate cells, and the supernatants mixed 48 hours later
[†] A variety of mixing conditions were tested, including preincubation for various times up to 2 hr at 37° C., 20° C., or 4° C. in the presence or absence of 10 mM $CaCl_2$. The value reported in this table is representative of the data obtained.

In Table 1, Coagulation Time and Activity were obtained as follows: Aliquots of 75 μL of media, conditioned by the growth of COS7 cells transfected with the indicated plasmids or mock transfected, were assayed for their ability to decrease the prolonged partial thromboplastin time of Factor VIII:C-deficient plasma in the one-stage assay. Briefly, 75 μL of Platelin (General Diagnostics) was incubated for 3 min at 37° C., followed by the addition of 75 μL of Factor VIII:C-deficient plasma plus 75 μL of the test sample for an additional 5 min incubation at 37° C. A 75 μL aliquot of prewarmed 0.025M $CaCl_2$ was added, and the clotting time measured with a Becton-Dickinson fibrometer. Normal human plasma diluted in COS7 cell medium was used as a standard. One mU of activity is assumed to correspond to approximately 100 pg of Factor VIII:C protein (Fay et al, *Proc Nat Acad Sci USA* (1982) 79:7200).

In Table 1, the COATEST assay (Kabi) was used to measure the generation of activated Factor X (Xa) as a linear function of the concentration of Factor VIII:C. The concentration of Factor Xa is measured by the proteolytic cleavage of the chromogen para-nitroaniline from a synthetic peptide substrate for Factor Xa. Normal human plasma diluted in 50 mM Tris-HCl, pH 7.3, 0.2% BSA was used as the standard.

For the RIA assay in Table 1, purified canine Factor VIII:C-inhibitory IgG was coated onto the wells of a 96-well polystyrene microtiter plate at a concentration of 3.5 μg/mL in 0.1M sodium carbonate buffer, pH 9.8, by overnight incubation at 37° C. The plates were washed 3 times with 0.1M NaCl, 0.05% Tween® 20 followed by incubation with a mixture of test medium samples and iodinated FVIII:C $M_r$ 92 K protein, both diluted in 0.05M imidazole, 0.1M NaCl, 1% bovine serum albumin, 0.05% Tween® 20, pH 7.3. The FVIII:C $M_r$ 92 K protein was isolated from plasma and was greater than 50% homogeneous as estimated by SDS-PAGE and silver staining. After incubation for 16 hr at room temperature, the plates were washed, and the amount of $^{125}I$ in the individual wells was measured in a gamma counter. An intermediate purified commercial Factor VIII:C preparation (Factor VIII, NORDISK) with a specific activity of 0.5 unit of coagulation activity per mg was used as the standard. This standard was calibrated against the World Health Organization Third International Factor VIII:C standard. We defined our intermediate purified standard to contain a $M_r$ 92 K RIA activity/Factor VIII:C coagulation activity ratio of 1.

For the ELISA assay in Table 1, purified human Factor VIII:C-inhibitory IgG was coated onto the wells of a 96-well PVC microtiter plate at a concentration 4.5 μg/mL in 0.1M sodium carbonate, pH 9.8, by overnight incubation at 37° C. The wells were washed as above and peroxidase-conjugated $F(ab')_2$ fragments of the human inhibitory IgG diluted in 0.1M imidazole, 0.15M NaCl, 1% BSA, 0.05% Tween® 20, pH 7.3, were added for a final incubation of 16 hr at room temperature. The color was developed with o-phenylenediamine solution. Normal human serum was used as a standard.

To verify that the observed coagulation activity was due to Factor VIII:C, the sensitivity of the coagulation to inhibition by antibody specific for Factor VIII:C was determined. Prior to assay, aliquots of conditioned media were preincubated for 2 hr at 37° C. in the presence of dilutions of normal human serum or of serum from a hemophiliac who had developed a high titer of inhibitory antibodies to Factor VIII:C. As shown in Table 2, the activity of the complete molecule, as well as that of the $M_r$ 92 K-80 K complex was reduced specifically by the inhibitory serum. The same results were obtained using three different inhibitory monoclonal antibodies which bind to the $M_r$ 80 K species. Inhibition of Factor VIII:C activity using inhibitory serum was studied as follows: 160 μL of the indicated COS7 cell conditioned medium were incubated with 20 μL of a 100-fold dilution of human Factor VIII:C inhibitory serum (Bethesda titer 1500 units) or a similar dilution of pooled normal human serum, or buffer alone (50 mM imidazole, 0.1M NaCl, 100 μg/=L BSA pH 7.3) for 2 hr at 37° C. These samples were then assayed for residual coagulation activity as outlined above.

TABLE 2

Coagulation Inhibition Assay

| Plasmid | serum | Coagulation Time (secs) |
|---|---|---|
| pSVF8-80 + pSVF8-92 | Normal | 51.9 |
|  | Immune | 74.5 |
|  | Buffer | 54.4 |
| pSVF8-200 | Normal | 46.4 |
|  | Immune | 69.4 |
|  | Buffer | 46.8 |

The inhibition experiment was repeated using monoclonal antibodies, as follows: 100 μL of conditioned medium were incubated for 2 hr at 37° C. with either 10 μL of a 1 μg/μL solution of anti-Factor VIII:C monoclonal antibody from Hybritech (Bethesda titer 14,000 units) or buffer, and then assayed as above. The results are shown in Table 3.

TABLE 3

Coagulation Inhibition Assay

| Plasmid | serum | Coagulation Time (secs) |
|---|---|---|
| pSVF8-92 + pSVF8-80 | Immune | 72.9 |
|  | Buffer | 48.0 |
| pSVF8-200 | Immune | 60.9 |
|  | Buffer | 44.9 |

To demonstrate more clearly the existence of a two chain complex, the active species was partially purified from the COS7 cell media by passage over a MAb column specific for the $M_r$ 80 K portion. As shown in Table 4, approximately 65% of the applied activity was retained by the column and 50% of this bound material was eluted in an active form and at a fivefold greater concentration than in the initial media. Thus an active complex can be isolated by affinity chromatography using an antibody specific for only the $M_r$ 80 K species. 100 μg of an anti-80 K monoclonal antibody (56 IgG) (Nordfang et al, *Thromb Haemostasis* (1985) 53.346) coupled to Sepharose® CL4B were incubated overnight at 20° C. with 1.4 mL of medium containing a total of 6.2 mU of activity (measured by the COATEST Assay obtained from COS7 cells cotransfected with pSVF8-92 and pSVF8-80 plasmids). After incubation, the slurry was loaded into a column and the flowthrough fraction was collected. The column was washed with 300 μL of Buffer A (50 mM imidazole, 0.1M NaCl, 0.1% sodium insulin, 0.2% NaN$_3$, pH 7.3) and then eluted with 300 μL of Buffer B (2.5M NaCl, 50% ethylene glycol, 0.5M imidazole, 0.1M CaCl$_2$, 0.1% sodium insulin, 0.2% NaN$_3$, pH 7.3).

TABLE 4

Partial Purification of $M_r$ 92 K-80 K Coagulation Active Complex

| Fraction | COATEST U/mL | 80 K ELISA U/mL |
|---|---|---|
| Media | .0044 | 0.175 |
| Flowthrough | .0017 | 0.13 |
| Eluate | .0200 | 0.76 |

Results reported here demonstrate that expression of the linker ("B") region, containing 918 amino acids or about 40% of the total for the intact protein, is not required for Factor VIII:C activity. Co-expression of individual $M_r$ 92 K and $M_r$ 80 K regions results in a level of Factor VIII:C activity comparable to that obtained from the expression of the whole Factor VIII:C coding region. These proteins assemble in vivo to form an active complex linked by a calcium bridge. The assembly does not require the presence of the B region and occurs efficiently for the two chains expressed in trans.

It is evident from the above results that Factor VIII:C activity can be achieved by directly producing an N-terminal fragment and a C-terminal fragment which are independently expressed, each having its own signal sequence. Thus, Factor VIII:C can be obtained more efficiently, since the large precursor need not be cloned and used as the coding sequence for the Factor VIII:C activity. Thus, cells may be employed for expression of Factor VIII:C which may be deficient in the capability for proper maturation of the full-length Factor VIII:C protein.

Example 2

Expression of the $M_r$ 92 K protein in COS7 cells using the pSVF8-92 construction was low compared to the amount of $M_r$ 80 K protein produced. The $M_r$ 92 K protein is apparently retained and/or degraded in the Golgi pathway, and is not efficiently processed or exported. Accordingly, the construction was modified in an attempt to increase the level of $M_r$ 92 K protein. Modifications of the following types were made: Changes in the 5' untranslated sequence of the Factor VIII:C gene; inclusion of heterologous 5' untranslated and leader sequences; and changes in the 3' untranslated sequences. These constructs are summarized below.

(A) 5' Untranslated Region Modifications

Plasaid pSVF8-92B. This plasmid is a derivative of pSVF8-92 in which the 30 bp of 5' untranslated sequence of pSVF8-92 is replaced with the entire 5' untranslated region of human Factor VIII:C cDNA (nucleotides 1 to 171; see FIG. 8 of Truett et al, supra), with a deletion of the G-C tails (by in vitro site-specific mutagenesis), and the three base changes shown below at the starting ATG (at position +172, FIG. 8, Truett et al, supra) to conform to Kozak's preferred sequences for efficient message translation in eukaryotic cells:

Factor VIII:C: GTCATG CAA (SEQ ID NO: 10)

Kozak consensus: ACCATG G (SEQ ID NO: 11)

This change alters the second amino acid of the signal peptide to Glu from Gln.

Plasmid PSVF8-92E. This plasmid is a derivative of pSVF8-92B in which the polylinker derived from pSV7d 5' to the Factor VIII:C sequences is removed with the exception of the SalI site, and the ATG codon in the 5' untranslated region (at 41 according to Truett et al, supra) is altered to ATT, by in vitro mutagenesis.

(B) Addition of Heterologous 5' Sequences

Plasmids PSVF8-92G, H, and I. These plasmids are derivatives of pSVF8-92B in which the 5' untranslated region as well as the natural Factor VIII:C signal sequences are replaced with the analogous region from the human tissue plasminogen activator (tPA) cDNA. In pSVF8-92G the first 35 amino acids (signal and pro-sequences) of the tPA pre-pro region are joined to mature Factor VIII:C $M_r$ 92 K with a serine substituted for the first amino acid (alanine) of the $M_r$ 92 K protein. In pSVF8-92H the first 32 amino acids of the tPA pre-pro region are joined to mature Factor VIII:C $M_r$ 92 K protein. In pSVF8-92I, the first 23 amino acids of the tPA pre-pro region are joined to mature Factor VIII:C $M_r$ 92 K protein. The tPA sequences are the same as those described for pSVF8-80.

Plasmid pSVF8-92J. This plasmid is a derivative of pSVF8-92G in which the tPA 5' region is replaced with 75 bp of Herpes simplex virus-1 (HSV-1) gD 5' untranslated sequences and 75 bp of HSV-1 gD signal sequence. pSVF8-92J also lacks the Ala→Ser substitution (R. J. Watson et al, *Science* (1982) 218:381–384).

(C) 3' Untranslated Region Changes

Plasmid pSVF8-92C. This plasmid is a variation of pSVF8-92B in which the $M_r$ 92 K coding region is fused directly to the translational stop codon and natural 3' untranslated sequences of human Factor VIII:C cDNA.

Plasmid pSVF8-92L. This plasmid is a derivative of pSVF8-92C in which the 3' untranslated region of pSVF8-92C is replaced with the 3' untranslated region of pSVF8-80.

(D) Results

Each of the plasmids of parts A–C above was transfected into COS7 cells along with pSVF8-80 as described in Example 1 and the media tested for Factor VIII:C activity as in Example 1(F).

Plasmid pSVF8-92B, the first tested, showed activity levels ranging from 2-to-8-fold better than pSVF8-92. Of the remaining plasmids pSVF8-92E appeared to be the best, being 1.65-fold better than pSVF8-92B. pSVF8-92J and I also produced substantially higher expression levels than pSVF8-92, being close to that of pSVF8-92E. The expression level of pSVF8-92G approximated that of pSVF8-92, whereas that of pSVFS-92H was substantially less than pSVF8-92. The expression levels of both pSVF8-92C and pSVF8-92L appear to be equivalent to that of pSVF8-92E.

Example 3

This example describes the preparation of constructs for producing polypeptides that consist of the $M_r$ 92 K chain and a portion of the B domain. These derivatives were made in an attempt to develop a heavy chain that is more stable and/or assembles more efficiently into an active complex with the light chain. The derivatives were chosen to mimic molecular species that have been observed in plasma-derived preparations of Factor VIII:C and in cell lysates and conditioned media from cells expressing recombinant full-length Factor VIII:C. Polypeptides of approximately the same size could possibly arise by thrombin cleavages of full-length Factor VIII:C.

(A) pSVF8-92S: This plasmid encodes a 982 amino acid heavy chain and was prepared from a full-length cDNA plasmid pSVF8-302 by cleavage at the first SacI site of the B-domain coding region. An oligonucleotide adaptor was used to install a translational stop codon and fuse the coding sequence to the natural human Factor VIII:C 3' untranslated sequence beginning at the first BalI site. This plasmid encodes the first 978 amino acids of native human Factor VIII:C and 4 substituted amino acid residues at the carboxy terminus.

(B) pSVF8-160: This plasmid provides a 1323 amino acid heavy chain and was prepared from a full-length clone (designated pSVF8-303) similar to pSVF8-200, but having the 5' untranslated region of pSVF8-92E. pSVF8-303 was cleaved with EcoRV and SmaI, and the blunt ends were ligated together to form pSVF8-160. This plasmid encodes the first 1315 amino acids of Factor VIII:C. Eight substituted amino acids are added at the carboxyl terminus as a result of the fusion of the polylinker of the vector pSV7d.

(C) pSVF8-170: This plasmid provides a 1416 amino acid heavy chain and was also prepared from pSVF8-303. pSVF8-303 was partially digested with BglII, and the resulting 6811 bp fragment was gel isolated and the ends ligated together to form pSVF8-170. This plasmid encodes the first 1405 amino acids of Factor VIII:C and has a carboxyl extension of 11 amino acids due to fusion of the polylinker of the vector pSV7d.

(D) pSVF8-120: This plasmid provides a 1107 amino acid heavy chain and was prepared from pSVF8-303. The plasmid pSVF8-303 was digested with ApaI and the cohesive ends were filled in with T4 polymerase. The resulting molecule was further digested with SmaI, the DNA self-ligated and propagated in *E. coli* HB101. This plasmid encodes 1102 amino acids from the amino terminus of Factor VIII:C plus an additional 5 amino acids at the carboxyl terminus, encoded by the pSV7d polylinker.

(E) Results

Each of the plasmids of parts A–D was transfected into COS7 cells along with pSVF8-80, and the media tested for Factor VIII:C activity, as described in Example 1.

All of these plasmids showed substantially reduced expression levels compared to that of pSVF8-92E. Interestingly, though, the ratio of RIA to COATEST activity for pSVF8-160 and pSVF8-170 is about 1.8, compared to 7.2 for pSVF8-92E. This result suggests that these longer heavy chain derivatives have a higher specific activity, that is, they are more efficiently assembled into active subunit complexes than the $M_r$ 92 K molecule itself. Also, the ratio of coagulation activity to COATEST activity is lower for the longer heavy chains at about 1.7 compared to 2.3 for $M_r$ 92 K and 1.35 for the complete molecule, suggesting that these longer polypeptides form complexes which are not as activated as that of the $M_r$ 92 K+$M_r$ 80 K complex.

Example 4

This example describes the preparation of stable CHO cell lines that produce the Factor VIII:C $M_r$ 92 K-80 K chain complex.

(A) Preparation of a Plasmid Encoding a Selectable Marker

The plasmid pAd-DHFR, bearing the murine DHFR cDNA, was constructed by fusing the major late promoter from adenovirus-2 (Ad-MLP, map units 16–27.3) to the 5' untranslated sequences of the mouse DHFR cDNA (J. H. Nunberg et al, *Cell* (1980) 19:355–64). SV40 DNA encoding part of the early transcription unit, including the intron of the small t antigen gene, and having the SV40 early region transcriptional termination region, was obtained from pSV2-neo (Southern and Berg, *J Mol Appl Gen* (1982) 1:327–41) and fused to the 3' untranslated end of the DHFR cDNA. These three segments were subcloned into pBR322 to obtain plasmid pAd-DHFR.

(B) Transfection and Culture of CHO Cells

CHO-DUKX-B11 cells carrying non-functional genes for dihydrofolate reductase (Urlaub and Chasin, *Proc Nat Acad Sci USA* (1980) 77:4216–4220) were transfected with a calcium phosphate coprecipitate of three plasmids: pSVF8-92C, pSVF8-92E, or pSVF8-80, and pAd-DHFR following the method of Graham and Van der Eb, supra, and modifications described by Wigler et al, *Cell* (1978) 14:725–731 and Lewis et al, *Somatic Cell Genet* (1980) 6:333–347. Coprecipitates contained up to 10 μg of each plasmid. Cells were selected for expression of the DHFR (positive) phenotype in a medium deficient in hypoxanthine and thymidine.

After isolation of DHFR positive clones and identification of those producing Factor VIII:C activity, the resulting cell lines were grown in methotrexate to amplify the DHFR genes and coamplify the Factor VIII:C genes. This selection was performed by plating cells in medium containing methotrexate in concentrations ranging from 0.025 to 0.2 μM. Methotrexate resistant clones were again assayed for Factor VIII:C activity.

(C) Assay Methods

Conditioned media from these DHFR positive clones were assayed by ELISA for Factor VIII:C light chain immunoreactivity by the method of Nordfang et al, *Thromb Haemostas* (1985) 53:346–50. Factor VIII:C heavy chain immunoreactivity was evaluated using a radioimmunoassay (RIA) described by R. L. Burke et al, *J Biol Chem* (1986) 261:12574–78. Active Factor VIII:c complexes formed by co-expression of the 92 K and 80 K $M_r$ glycoproteins were measured using the COATEST assay described in Example 1.

(D) CHO Lines Expressing Active 92 K-80 K $M_r$ Complexes

Shown in Table 5 are four independent CHO cell lines that simultaneously express products of all three plasmids used for transfection. The Factor .VIII:C activity values shown in Table 5 are those initially observed. Expression of glycoproteins by stable cell lines usually improves after passage in T-75 flask cultures. An example of this can be seen for the line 10-C2, which ultimately produced 200 mU Factor VIII:C activity per mL conditioned medium (Table 6). Cloning these stable cell lines illustrates that the independently expressed heavy and light chains of Factor VIII:C can assemble into an active complex and be secreted by Chinese hamster ovary cells.

TABLE 5

CHO cell lines producing active 92 K-80 K complexes

| Clone | Transfected DNA | mU COATEST/mL |
|---|---|---|
| 11-D6 | pSVF8-92C, pSVF8-80, pAd-DHFR | 43 |
| 11-D5 | PSVF8-92C, pSVF8-80, pAd-DHFR | 30 |
| 8-C1 | PSVF8-92E, pSVF8-80, pAd-DHFR | 18.2 |
| 10-C2 | pSVF8-92E, pSVF8-80, pAd-DHFR | 70.0 |

That the three plasmids were integrated into the chromosomes of the CHO cells is suggested by the fact that the cell lines of Table 5 could be grown for many passages without loss of Factor VIII:C expression. It was then necessary to determine if expression of Factor VIII:C glycoproteins could be co-amplified by methotrexate selection. All four of these cell lines were placed under selection in several concentrations of methotrexate. Resistant colonies (DHFR genes amplified) were obtained for each line and these were screened for Factor VIII:C activity. Expression of Factor VIII:C was lost or unchanged in methotrexate resistant 11-DS and 11-D6 clones. Expression of Factor VIII:C varied among methotrexate resistant clones derived from 10-C2 and 8-C1 (shown in Table 6).

Twenty-two methotrexate-resistant 8-C1 clones were examined, the data for 10 of which are reported in Table 6. The amount of Factor VIII:C amplification varies among clones, suggesting that either one of the subunit genes may have been co-amplified with the DHFR cassette, or both of them, or neither one. Note clones 8C1-A2, 8C1-C2, and 8C1-C5 as examples of these four possibilities. Similarly, 30 methotrexate-selected derivatives of 10-C2 were evaluated, the data for 20 of which are also represented in Table 6. These also contain a spectrum of activity. Note clones 10C2-A2, 10C2-D2, 10C2-B5, and 10C2-C6 as examples of the four different co-amplification possibilities.

TABLE 6

| Clone | conc. MTX (μM) | COATEST (mU/mL) | LC-ELISA (mU/mL) | HC-RIA (mU/mL) |
|---|---|---|---|---|
| 8-C1 | 0 | 18 | 1275 | n.d. |
| 8C1-A1 | 0.1 | <50 | 1750 | 80 |
| 8C1-A2 | 0.1 | 60 | 1950 | >1000 |
| 8C1-A5 | 0.05 | 2 | 100 | 10 |
| 8C1-B3 | 0.025 | 33 | 1950 | 1000 |
| 8C1-B4 | 0.025 | 50 | 3550 | 820 |
| 8C1-B5 | 0.025 | 35 | 1950 | >1000 |
| 8C1-C2 | 0.025 | 130 | 13,100 | >>1000 |
| 8C1-C3 | 0.025 | 165 | 3900 | >>>1000 |
| 8C1-C5 | 0.025 | 30 | 1750 | 760 |
| 10-C2 | 0 | 200 | 1400 | 700 |
| 10C2-A1 | 0.05 | 61 | 1600 | 400 |
| 10C2-A2 | 0.1 | 67 | 6700 | 700 |
| 10C2-A4 | 0.05 | 63 | 2250 | 1200 |
| 10C2-A5 | 0.05 | 183 | 9450 | 2660 |
| 10C2-A6 | 0.05 | 320 | 8600 | 7400 |
| 10C2-B1 | 0.05 | 408 | 8100 | 4300 |
| 10C2-B3 | 0.05 | 134 | 800 | 9800 |
| 10C2-B4 | 0.05 | 394 | 18,000 | 7800 |
| 10C2-B5 | 0.05 | 461 | 15,000 | 8400 |
| 10C2-B6 | 0.05 | 247 | 2200 | 9800 |
| 10C2-C1 | 0.1 | 160 | 8100 | 7600 |
| 10C2-C2 | 0.05 | 228 | 6000 | 5600 |
| 10C2-C3 | 0.05 | 294 | 14,850 | 2650 |
| 10C2-C5 | 0.05 | 294 | 12,400 | 5400 |
| 10C2-C6 | 0.05 | 100 | 1350 | 520 |
| 10C2-D2 | 0.05 | 496 | 1560 | 16,400 |
| 10C2-D3 | 0.05 | 242 | 10,200 | 2260 |
| 10C2-D4 | 0.05 | 165 | 14,100 | 3500 |
| 10C2-D5 | 0.05 | 316 | 7800 | 5200 |
| 10C2-D6 | 0.05 | 141 | 1600 | 6400 |

Among the CHO lines described in Table 6 is one (10C2-D2) that produces 0.5 U/mL of active Factor VIII:C complex, which is one half the concentration found in normal human plasma. For analysis and purification of Factor VIII:C material, CHO cell lines expressing Factor VIII:C polypeptides were grown in laboratory scale fermentations to produce 1–2 liter quantities of tissue culture fluid. Assay of this material showed that approximately 10% to 20% of immunoreactive Factor VIII:C from unamplified lines is active in the COATEST. In amplified lines, the percentage of active material drops to 2% to 5% of the total immunoreactive product. This means that only a fraction of the heavy and light chains of FVIII:C is assembled into active complexes. The remainder may exist as free subunits or in degraded forms.

Plasmids pSVF8-92 and pSVF8-80 were deposited at the American Type Culture Collection (ATCC) on Jan. 24, 1986 and given ATCC Accession Nos. 40222 and 40223, respectively. Plasmid pSVF8-200 was deposited at the ATCC on Jul. 17, 1985 and was given ATCC Accession No. 40190.

Example 5

This example describes modification of the plasmid pSVF8-80 to correct the amino terminal amino acid of the FVIII:C light chain glycoprotein. A consequence of engineering, which provided the signal peptide needed for independent secretion of the 80 K $M_r$ glycoprotein (Example 1) is the substitution of Ser for the normal aminoterminal residue of human plasma FVIII:C light chains. New plasmids were made in an attempt to change the tPA pre-pro peptide sequence, so that the FVIII:C light chain will have the Glu residue at its amino terminus instead of the mutant Ser residue after proteolytic processing.

The FVIII:C light chain is thought to be cleaved from the full-length FVIII:C precursor before secretion, i.e.

intracellularly, by a protease resident in the Golgi apparatus. This cleavage occurs between amino acid residues 1648 and 1649 (Arg-Glu). On polyacrylamide gels the light chains appear as a doublet of 77 and 80 K $M_r$ bands, representing polypeptides having one or two N-linked oligosaccharides. Independent secretion of light chains was achieved by fusion of the light chain coding region of the FVIII:C cDNA to the cDNA of tPA. In the process of supplying the tPA signal peptide, however, the amino terminus of the FVIII:C light chain was mutated from the native glutamic acid residue to a serine. Although this mutant recombinant light chain displays molecular characteristics similar to the chain derived from full-length recombinant FVIII:C, there is preliminary evidence that 1) it may not be alternatively glycosylated in the same manner as the chain cleaved from the FVIII:C precursor, 2) it may behave differently during purification by ion exchange and vWF Sepharose® chromatography, and 3) it may be different antigenically from authentic light chain.

The tPA pre-pro peptide sequence requires three proteolytic cleavages to release the mature polypeptide. Shown below is the translation of the protein coding sequence of pSVF8-80 in the region of the tPA-FVIII:C 80 K fusion:

The signal peptidase cleavage has been thought to occur on the carboxy side of either Ser (position -13) or Ala (position -8), indicated by asterisks. The second cleavage probably occurs on the carboxy side of Arg (position -4, indicated by @ above). The third processing event is proteolysis at the Arg-Ser bond to release a Gly-Ala-Arg tripeptide and leave a Ser (position 1) aminoterminus on the mature tPA or FVIII:C light chain polypeptides.

(A) Preparation of Plasmids (1) pSVF9-80KG

The Ser codon (position 1) was changed by site-directed mutagenesis to a Glu codon (position 1). This was done in an effort to allow the first two proteolytic processing events to occur normally, and test whether the Arg-Glu protease could recognize and cleave the dipeptide in an altered context, i.e., where the tPA tripeptide is substituted for the FVIII:C B domain. The tPA-80 K chain fusion region is shown below. Otherwise, this plasmid is identical to pSVF8-80.

```
pSVF8-80:

-35                     -30                      -25
    Met Asp Ala Met Lys Arg Gly Leu Cys Cys Val Leu Leu Leu
    ATG GAT GCA ATG AAG AGA GGG CTC TGC TGC TGT GTG CTG CTG

-20                     -15    *            -10    *
    Cys Gly Ala Val Phe Val Ser Pro Ser Gln Glu Ile His Ala
    TGT GGA GCA GTC TTC GTT TCG CCC AGC CAG GAA ATC CAT GCC

-5  @               1               5
    Arg Phe Arg Arg Gly Ala Arg Ser Ile Thr Arg Thr Thr Leu
    CGA TTC AGA AGA GGA GCC AGA TCT ATA ACT CGT ACT CTT CAG

10
    Gln Ser Asp
    CAG TCT GAT  (SEQ ID NOS: 12—13)
```

```
pSVF8-80KG:

-35                     -30                      -25
    Met Asp Ala Met Lys Arg Gly Leu Cys Cys Val Leu Leu Leu
    ATG GAT GCA ATG AAG AGA GGG CTC TGC TGC TGT GTG CTG CTG

-20                     -15    *            -10    *
    Cys Gly Ala Val Phe Val Ser Pro Ser Gln Glu Ile His Ala
    TGT GGA GCA GTC TTC GTT TCG CCC AGC CAG GAA ATC CAT GCC

-5  @               1               5
    Arg Phe Arg Arg Gly Ala Arg Glu Ile Thr Arg Thr Thr Leu
    CGA TTC AGA AGA GGA GCC AGA GAA ATA ACT CGT ACT CTT CAG

10
    Gln Ser Asp
    CAG TCT GAT  (SEQ ID NOS:14—15)
```

(2) pSVF8-80S

Twelve codons were deleted from pSVF8-80 by in vitro mutagenesis, and the Ser (position 1) codon changed to a codon for Glu. This placed the Glu FVIII:c light chain residue after Ser23 of the putative tPA signal peptide (indicated by an asterisk). Cleavage by signal peptidase on the carboxy side of Ser23 releases the non-mutant FVIII:C light chain. The tPA—80 K chain fusion region of pSVF8-80S is shown below. Otherwise this plasmid is identical to pSVF8-80.

```
pSVF8-80S:

-23              -20                 -15                 -10
    Met Asp Ala Met Lys Arg Gly Leu Cys Cys Val Leu Leu Leu
    ATG GAT GCA ATG AAG AGA GGG CTC TGC TGC TGT GTG CTG CTG

-5                   *   1               5
    Cys Gly Ala Val Phe Val Ser Pro Ser Glu Ile Thr Arg Thr
    TGT GGA GCA GTC TTC GTT TCG CCC AGC GAG ATA ACT CGT ACT

10
    Thr Leu Gln Ser Asp Gln Glu Glu Ile Asp Tyr Asp Asp Thr
    CTT CAG CAG TCT GAT CAA GAG GAA ATT GAC TAT GAT GAT ACC  (SEQ ID NOS:16—17)
```

(3) pSVF8-80R

A deletion of three codons of pSVFS-80, to remove the tPA pro-tripeptide, was made by in vitro mutagenesis, and the Ser (position 1) codon was changed to one for Glu. This places a Glu residue after Arg32 of the tPA pro-peptide, marked with @ on the tPA-80 K chain fusion region of pSVF8-80R shown below:

This construction was made in the hope that cleavage by a Golgi-resident protease with dibasic specificity would release FVIII:C light chains having Glu amino termini.

(4) PSVF8-80A

Seven codons of pSVF8-80 were deleted by site-directed mutagenesis, removing the DNA encodina the putative tPA pro sequence, and the Ser (position 1) codon was replaced by a Glu codon after codon 28 (Ala) of the putative tPA signal peptide coding sequence (indicated by an asterisk below). Cleavage by signal peptidase on the carboxy side of Ala$_{28}$ will release non-mutant FVIII:C light chain. The tPA-80 K chain fusion region is shown below. Otherwise, this plasmid is identical to pSVF8-80.

```
pSVF8-80R:

-32         -30                 -25                 -20
    Met Asp Ala Met Lys Arg Gly Leu Cys Cys Val Leu Leu Leu
    ATG GAT GCA ATG AAG AGA GGG CTC TGC TGC TGT GTG CTG CTG

-15                 -10                 -5
    Cys Gly Ala Val Phe Val Ser Pro Ser Gln Glu Ile His Ala
    TGT GGA GCA GTC TTC GTT TCG CCC AGC CAG GAA ATC CAT GCC

@   1                               10
    Arg Phe Arg Arg Glu Ile Thr Arg Thr Thr Leu Gln Ser Asp
    CGA TTC AGA AGA GAG ATA ACT CGT ACT CTT CAG CAG TCT GAT  (SEQ ID NOS:18—19)
```

```
pSVF8-80A:

-28             -25                 -20                 -15
    Met Asp Ala Met Lys Arg Gly Leu Cys Cys Val Leu Leu Leu
    ATG GAT GCA ATG AAG AGA GGG CTC TGC TGC TGT GTG CTG CTG

-10                 -5                  *
    Cys Gly Ala Val Phe Val Ser Pro Ser Gln Glu Ile His Ala
    TGT GGA GCA GTC TTC GTT TCG CCC AGC CAG GAA ATC CAT GCC 1                                   10
    Glu Ile Thr Arg Thr Thr Leu Gln Ser Asp Gln Glu Glu Ile
    GAG ATA ACT CGT ACT CTT CAG CAG TCT GAT CAA GAG GAA ATT  (SEQ ID NOS:20—21)
```

(B) Expression and Protein Sequence Analysis (1) Transfection into COS7 Cells

COS7 cells were transfected using the DEAE-dextran procedure described in Example 1, and conditioned media were assayed by the LC-ELISA. All four derivatives of pSVF8-80 encode 80 K $M_r$ glycoproteins that are reactive in the LC-ELISA and that can be immunoprecipitated after biosynthetic radiolabeling with various anti-FVIII:C light chain antibodies. Except for pSVF8-80R, all the derivatives lead to secretion of about the same amount of 80 K glycoprotein as pSVF8-80. Secretion of 80 K glycoprotein from cells transfected with PSVF8-80R is very poor, usually less than 25% of that produced from the other plasmids. In addition, the appearance of this FVIII:C light chain is different on gel electrophoresis, where the bands are always diffuse.

(2) Expression in CHO Cells

Each of these plasmids was introduced into DUKX-B11 CHO cells with pAd-DHFR as described in Example 4. Permanent cell lines were established for production of each type of light chain. Expression of the 80 K $M_r$ glycoproteins in CHO cells is very similar to expression in COS7 cells, with respect to the amounts of glycoprotein secreted and the appearance of the 80 K bands on gel electrophoresis. CHO lines transfected with pSVF8-80R produced such a low level of 80 K glycoprotein that analysis of this material was not done.

temperature, 1 mL of gel per 1000 units FVIII-LC. The gel was then packed into a column and washed with 20 column volumes of a low salt buffer (0.05M imidazole, 0.15M NaCl, 0.01M $CaCl_2$, 10% glycerol, 0.02% $NaN_3$, pH 7.3), followed by 20 column volumes of a high salt buffer (0.05M imidazole, 1.0M NaCl, 10% glycerol, pH 7.3). FVIII-LC was eluted from the immunosorbent using 1M CaCl in 0.05M imidazole, 0.15M NaCl, 10% glycerol after one hour incubation. The eluate was immediately desalted on a Sephadex® G-25 column to a solution of 0.05M imidazole, 0.15M NaCl, 0.01M $CaCl_2$, 10% glycerol, 0.02% Tween® 80, 0.02% $NaN_3$, pH 7.3 and stored at −80° C. N-terminal sequence analysis was performed on an Applied Biosystem 477A sequencer.

The results of this analysis are shown in Table 7. The 80 K glycoprotein encoded by pSVF8-80KG has a tripeptide extension on its aminoterminus. Presumably this is the tPA pro tripeptide Gly-Ala-Arg, which cannot be processed by the Arg-Glu protease that recognizes the FVIII:C B domain. Further, the N-terminal sequences reveal that the signal peptide of tPA is actually 22 amino acid residues in length, with signal peptidase cleavage occurring on the carboxy side of $Pro_{22}$. Therefore, plasmid constructions pSVF8-80S and pSVF8-80A, predicated upon signal peptidase cleavage after $Ser_{23}$ and $Ala_{28}$, respectively, lead to incorrect amino terminal residues on the 80 K light chains.

TABLE 7

N-terminal Sequences of 80 K Chains with Modified tPA pre-pro Regions

| Plasmid | N-terminal Sequence | Amount (pmol) |
| --- | --- | --- |
| pSVF8-80 | X-Ile-X-Arg-Thr-X-Leu-Gln-X-Asp-Gln- (SEQ ID NO:22) | 10 |
| pSVF8-80KG | X-X-Arg-Glu-Ile-Thr-Arg-Thr-Thr-Leu- (SEQ ID NO:22) | 20 |
| pSVF8-80S | Ser-Glu-Ile-Thr-Arg-Thr- (SEQ ID NO:24) | 40 |
| pSVF8-80A | X-Gln-Glu-Ile- (SEQ ID NO:25) | 40 |

3. Purification and Amino Acid Sequence Analysis

Conditioned media from either large scale COS7 transfections (pSVF8-80KG) or from transfected (amplified) CHO cell lines (pSVF8-80K cell line 1OC2B5; pSVF8-80A, cell line AlN; pSVF8-80S, cell line SiR) were prepared. The medium was DME H12 with 10% FBS. FVIII-LC was purified for sequencing by a two-step procedure comprising ion exchange chromatography followed by affinity chromatography. Ion exchange chromatography was performed as follows: A column of S-FF Sepharose® (15×0.8 cm) was equilibrated with 0.02M MES, 0.05M NaCl, 0.01M $CaCl_2$, pH 5.8, $\lambda_{20°\ C.}$=7.2 mS. Conditioned medium (500–1300 mL) was applied to the column after adjustment of pH to 5.8 with a flow rate of 100 mL/h. The column was washed with 10 column volumes of 0.05M imidazole, 0.05M NaCl, 0.01M $CaCl_2$, pH 7.35, $\lambda_{20°\ C.}$=8.8 mS at a flow rate of 200 mL/h. FVIII-LC was eluted by addition of 0.1M $CaCl_2$ to the washing buffer, flow rate 50 mL/h. All operations were performed at 4° C.

Affinity chromatography was performed as follows: The murine monoclonal anti-FVIII-LC antibody 56-IgG was coupled to Sepharose® 4B by the CNBr method to a density of 2.5 mg/mL gel. The FVIII-LC containing eluate was incubated with the immunosorbent overnight at room Results shown in this example reveal the difficulty of predicting how a secreted polypeptide will be processed following transcription and translation. Modifications of the protein sequence have unexpected consequences for proteolytic processing and oligosaccharide addition, and can affect the overall efficiency of secretion.

Example 6

This example describes a method for expression of authentic FVIII:C light chains using the signal peptide of human $\alpha_1$-antitrypsin.

A. Preparation of Plasmids 1. pSVα1AT.Met

A cDNA encoding the mature human $\alpha_1$-antitrypsin polypeptide had been assembled using fragments of human liver cDNA clones and a synthetic oligonucleotide; the assembly was ligated as a BamHi-SalI fragment into pBR322 to make plasmid pAT(Met) (Rosenberg et al, *Nature* (1984) 312:77–80). A synthetic oligonucleotide linker-adapter and part of a cDNA clone encoding the signal peptide were used to attach the signal peptide coding sequence, with an EcoRI restriction site on the 5' end, to the BamHI site of pAT(Met). The resulting 1271 bp EcoRI-SalI fragment, encoding the translated sequences of human $\alpha_1$-antitrypsin, was ligated into the EcoRI-SalI sites of pSV7d (described in Example 1) to make pSV$\alpha$1AT.Met.

2. pSVF8-80AT

Plasmid pSV$\alpha$1AT.Met was opened at the BamHI site, which occurs at the boundary between the codons of the signal peptide and mature $\alpha_1$-antitrypsin sequences. The cohesive end of this restriction site was removed with mung bean nuclease to leave the GAG (Glu) codon, and the $\alpha_1$-antitrypsin sequence was deleted by digestion with SalI. The coding sequence of FVIII:C 80 K was prepared for attachment by in vitro mutagenesis of codons 1 and 2 of pSVF8-80 to form an EcoRV site (which preserves codon 2 as an Ile codon). This allowed the FVIII:C light chain coding sequence (as an EcoRV-SalI sequence starting at codon 2) to be fused in correct reading frame to codon 1 of $\alpha_1$-antitrypsin, and replace the coding sequence of mature human $\alpha_1$-antitrypsin.

The coding sequence of pSVF8-80AT in the region of fusion is shown translated below. Except for substitution of the $\alpha_1$-antitrypsin signal peptide coding sequence for the tPA pre-pro coding sequence, this plasmid is identical to pSVF8-80.

8OAT directs the synthesis of FVIII:C light chains that appear as a doublet of 77–80 K $M_r$. The amount produced in COS7 cells is the same as for pSVF8-80. Co-expression with pSVF8-92C, or other FVIII:C heavy chain plasmid, leads to production of active PVIII:C complexes measured in the COATEST assay.

2. Purification and amino acid sequence analysis

Material for purification was prepared by transfection of COS7 cells in T-175 flasks, using increased cell density and decreased chloroquine diphosphate concentration. Conditioned media were collected 60 hours after transfection. Purification and amino acid sequence analysis were performed as described in Example 5. The results of aminoterminal sequence analysis (Table 8) indicate that the FVIII:C light chain encoded by pSVF8-80AT has the same aminoterminal sequence as authentic human plasma FVIII:C light chain.

```
pSVF8-80AT (amino terminal region):

-24                 -20                 -15                 -10
Met Pro Ser Ser Val Ser Trp Gly Ile Leu Leu Leu Ala Gly Leu
ATG CCC TCG AGC GTC TCG TGG GGC ATC CTC CTG CTG GCA GGC CTG

-5                  1                   5
Cys Cys Leu Val Pro Val Ser Leu Ala Glu Ile Thr Arg Thr Thr
TGC TGC CTG GTC CCT GTC TCC CTG GCT GAG ATC ACT CGT ACT ACT 10                  15                  20
Leu Gln Ser Asp Gln Glu Glu Ile Asp Tyr Asp Asp Thr Ile Ser
CTT CAG TCT GAT CAA GAG GAA ATT GAC TAT GAT GAT ACC ATA TCA    (SEQ ID NOS:26-27)
```

TABLE 8

N-terminal Sequence of 80 K Chains Secreted Using $\alpha_1$-antitrypsin Signal Peptide

| Plasmid | N-terminal Sequence | Amount (pmol) |
| --- | --- | --- |
| pSVF8-80 | X-Ile-X-Arg-Thr-X-Leu-Gln-X-Asp-Gln- | 10 |
| pSVF8-80AT | Glu-Ile-Thr-Arg-Thr-X-Leu-Gln-Ser-Asp-Gln | 10 |

B. Expression and Amino Acid Sequence Analysis

1. Expression of pSVF8-80AT in COS7 cells

COS7 cells were transfected with pSVF8-80AT and a heavy chain expression plasmid, usually pSVF8-92C. Conditioned media were assayed by LC-ELISA, HC-ELISA and COATEST. Transfected cells were also labeled with radioactive Met, so that the biosynthetically radiolabeled FVIII:C light chains could be immunoprecipitated and visualized after polyacrylamide gel electrophoresis. Plasmid SVF8-

3. In vitro assembly of 80AT FVIII:C light chains

The ability of 80 AT FVIII:C light chains to recombine with purified FVIII:C heavy chains in vitro was tested in an experiment shown in Table 9. Purified FVIII:C light chains were incubated at concentrations of 3.7 U/mL with purified recombinant (from full-length human FVIII:C) heavy chains at 17 U/mL in buffer containing 50 m $Mn^{++}$ and 150 $\mu$M $\beta$-mercaptoethanol. As the control, purified recombinant heavy and light chains were allowed toLreassociate under the same conditions, and the quantity of active FVIII:C produced was assayed by COATEST. These results suggest that the 8OAT FVIII:C light chain can be combined in vitro with purified recombinant heavy chain.

TABLE 9

Combination of Recombinant FVIII:C Light
Chains with Heavy Chains in vitro

| Purified FVIII-LC | Purified FVIII-HC | Percent Control Activity |
|---|---|---|
| 80AT | full-length | 86 |
| 80S | full-length | 51 |
| 80A | full-length | 92 |
| 80KG | full-length | 233 |

Example 7

This example describes plasmids for improved expression of the Factor VIII:C heavy chain. Modifications in DNA sequences responsible for the initiation of transcription and in non-coding sequences are made in order to increase the efficiency of transcription and the stability of the messenger RNA. The heavy chain glycoprotein is modified by a carboxy-terminal extension composed of segments of the B domain joined by a short peptide. This is done to obtain a heavy chain that is secreted from cells more efficiently, is more stable in tissue culture medium, and assembles more efficiently with the light chain.

A. Preparation of Plasmids 1. pCMVF8-92/6x

In an effort to improve the level of transcription and stability of the messenger RNA for the Factor VIII:C 92 K $M_r$ heavy chain, the SV40 early transcriptional initiation region was replaced by sequences from the human cytomegalovirus immediate early region (Boshart et al, Cell (1985) 4:521–530). In addition, 5' untranslated sequences contributed by the SV40 early region to the messenger RNA were replaced with the 5' untranslated sequences of the HCMV lEl gene, including its first intron. This intron is included on the assumption that spliced transcripts lead to faster processing and more stable mRNA. The expression vector also has an SV40 origin of replication to permit transient expression in COS7 cells, and a bacterial β-lactamase gene to permit DNA cloning by selection for ampicillin resistance.

The plasmid was constructed from a 700 bp SalI-PvuI fragment of pSV7d (described in Example 1) containing the SV40 polyadenylation region, a 1400 bp PvuI-EcoRI (filled in with Klenow polymerase) fragment of pSVT2 (Myers et al, Cell (1981) 25:373–84; Rio et al, Cell (1983) 32:1227–40) providing the SV40 origin of replication and the rest of the β-lactamase gene, a 1700 bp SspI-SalI fragment derived from a plasmid subclone of the human cytomegalovirus (Towne strain) in which the SalI site was introduced by in vitro mutagenesis near the translational start site for the lEl protein, and the 4300 bp SalI-SalI fragment of pSVF8-92C (described in Example 2) containing the cDNA encoding the Factor VIII:C 92 K $M_r$ glycoprotein.

2. pSVF8-92tβ

This plasmid is a derivative of pSVF8-92C that encodes the 92 K $M_r$ recombinant heavy chain with a C-terminal extension composed of N-terminal and C-terminal amino acid residues of the central (B) domain of the Factor VIII:C precursor linked by a peptide hinge peptide homologous to that of human immunoglobulin a heavy chain. It is composed of a 4900 bp HindIII-SalI fragment from pSVF8-92C, into which was inserted a 110 bp HindIII-SalI synthetic linker-adapter (shown below).

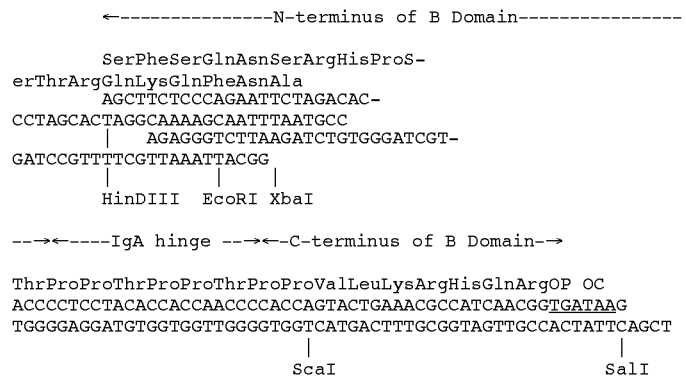

The linker-adapter encodes a carboxy-terminal extension of 34 additional amino acid residues, and one potential site of N-linked glycosylation. The C-terminal peptide should increase the molecular weight of the heavy chain to approximately 96 K $M_r$, and to about 99 K $M_r$ if it is glycosylated.

B. Assay for FVIII:C Heavy Chain Antigen and FVIII:C Complex Formation

The cofactor activity of the FVIII:C light chain-heavy chain complex was estimated using a commercially available test kit from KabiVitrum (COATEST). Immunoreactive FVIII:C light chain was measured by ELISA using HZ IgG coating antibody and peroxidase-conjugated antibodies from Nordisk Gentofte. The FVIII:C heavy chain immunoreactivity was quantified using an ELISA developed at Nordisk Gentofte, which employs human polyclonal antibody from an inhibitor patient (E-IgG).

C. Transient Expression of pCMVF8-92/6x

The pCMVF8-92/6x plasmid was cotransfected with various FVIII:C light chain plasmids (described in Example 5) into COS7 cells using the DEAE-dextran procedure. A sample of results from these transfections is shown in Table 10. The data suggest that addition of the CMV lEl promoter/enhancer, and the 5' untranslated sequences of the lEl gene yields a 2.5 fold improvement (on average) in FVIII:C heavy chain expression.

TABLE 10

Expression in COS7 Cells of
pCMVF8-92/6x Versus pSVF8-92C

| | | FVIII:C Activity (mU/mL) | |
|---|---|---|---|
| HC-Plasmid | LC-Plasmid | COA[a] | HC-RIA[b] |
| pSVF8-92C | pSVF8-80 | 46 | 160 |
| pSVF8-92C | -80A | 34 | 72 |
| pSVF8-92C | -80R | 61 | 310 |
| pSVF8-92C | -80S | 31 | 46 |
| pCMVF8-92/6x | -80 | 87 | 290 |
| pCMVF8-92/6x | -80A | 131 | 140 |
| pCMVF8-92/6x | -80R | 178 | 330 |
| pCMVF8-92/6x | -80S | 114 | 690 |

[a]COATEST assay
[b]Radioimmunoassay for heavy chain

D. Transient Expression in COS7 Cells of DSVF8-92tβ

Shown in Table 11 are the results of cotransfecting pSVF8-92tβ with a Factor VIII:C light chain expression plasmid (pSVF8-80AT, described in Example 6) into COS7 cells. The 92tβ heavy chain is secreted at higher levels than the 92C heavy chain, which has a single amino acid (Ser) carboxy-terminal extension. The ratio of COATEST (COA) activity to ELISA-reactive glycoprotein (a measure of complex formation) is greater for 92tβ chains than for 92C chains. In addition, the 92tβ heavy chain is secreted well in serum-free medium and appears to be stable, with a ratio of activity to protein nearly the same as in 10% FBS. These results show that this 34 amino acid carboxy-terminal extension improves secretion and stabilizes the recombinant FVIII:C heavy chain.

TABLE 11

Expression of pSVF8-92tβ in COS7 Cells

| | | | | mU/mL FVIII | | |
|---|---|---|---|---|---|---|
| Exp[†] | Medium | Plasmid 1 | Plasmid 2 | COATEST | LC[a] | HC[b] |
| 1 | 10% FBS | pSVF8-92tβ | pSVF8-80AT | 41 | 487 | 98 |
| | | pSVF8-92C | pSVF8-80AT | 23 | 442 | 49 |
| 2 | 10% FBS | pSVF8-92tβ | pSVF8-80AT | 80 | 484 | 162 |
| | | pSVF8-92C | pSVF8-80AT | 30 | 639 | 90 |
| 3 | HB CHO | pSVF8-92tβ | pSVF8-80AT | 38 | 262 | 125 |

[†]COS7 cell monolayers in duplicate were exposed to DNA in DEAE-Dextran, washed, and treated with medium containing chloroquine diphosphate for 8 hrs. Cells were washed to remove the drug, then covered with 5 mL DME H21 containing 10% FBS. For expression in serum-free medium, dishes were washed after 12–16 hrs. and overlaid with HB CHO ® from Hana Biologicals. Conditioned media were assayed for FVIII:C activity as described.
[a]by ELISA assay specific for light chain.
[b]by ELISA assay specific for heavy chain.

Example 8

This example describes a method for expression of a FVIII:C heavy chain having $Arg_{740}$ as the C-terminus.

A. Preparation of Plasmid pCMVF8-92R

The FVIII:C heavy chain encoded by the plasmid pCMVF8-92/6x has $Ser_{741}$ as a C-terminal extension. In order to obtain a FVIII:C heavy chain with $Arg_{740}$ as the C-terminus, a 1588 bp BamHI fragment of pCMVF8-92/6x, encoding the 3' end of the coding sequence derived from pSVF8-92C was purified. This fragment was cloned into m13mp18 and the $Ser_{741}$ residue was changed to a translational stop codon by in vitro mutagenesis. The pCMVF8-92R expression plasmid was assembled by cloning the mutagenized BamHI fragment into the 5840 bp BamHI fragment of the original vector. By this procedure 680 bp of FVIII:C 3' untranslated sequences were deleted.

B. Transient Expression in COS7 Cells of pCMVF8-92R

The pCMVF8-92R plasmid was co-transfected with the FVIII:C light chain plasmid pSVF8-80AT (described in Example 6) into COS7 cells using the calcium phosphate technique (Graham and van der Eb, *Virol* (1973) 52:456–67). The media were changed 18 and 42 hours post-transfection. Media samples for assays were collected 66 hours post-transfection. The results from these assays are shown in Table 12 below. The data shows that FVIII:C activity was generated when pCMVF8-92R was cotransfected with a plasmid providing expression of FVIII LC.

TABLE 12

Coexpression of pCMVF8-92R and pSVF8-80AT.

| Transfection | COA (mU/mL) | HC:Ag (mU/mL) | LC:Ag (mU/mL) |
|---|---|---|---|
| A | 243 | 400 | 990 |
| B | 263 | 460 | 1190 |

Example 9

This example describes the preparation of a stable CHO cell line that produces the native FVIII:C $M_r$ 92K-80K complex.

The DHFR⁻ CHO cell line DG44 (G. Urlaub et al, *Som Cell Mol Genet* (1986) 12:555–66) was first transfected with the plasmid pCMVF8-80AT. In this plasmid the CMV promoter (described in Example 7) regulates FVIII LC cDNA derived from pSVF8-80AT (described in Example 6), and downstream contains the Ad-MLP/dhfr cassette derived from pAd-DHFR (described in Example 4). The cells were transfected using the polybrene method described by W. Chaney et al, *Som Cell Mol Genet* (1986) 12:237–44. By selecting for DHFR+ cells (in DMEM+10% DFSC) several FVIII-LC producers were isolated; one of which was designated 11 W.

In order to introduce FVIII-HC into 11 W, the cell line was cotransfected with the plasmid pPR78 (this plasmid is analogous to pCMVF8-80AT, but contains the HC cDNA derived from pCMVF8-92R described in Example 8 instead of the LC cDNA) and pSV2-neo (P. J. Southern and P. Berg, *J Mol Appl Gen* (1982) 1:327–41). The transfection method used was the modified calcium phosphate procedure (G. Chen and H. Okayama, *Mol Cell Biol* (1987) 7:2745–52). Transfectants were isolated in medium containing 700 μg/mL Geneticin (G418 sulfate, Gibco). Cells from the primary pool were subcloned by limiting dilution, and individual clones tested for expression of active FVIII:C. In this way several FVIII:C producing cell lines were isolated, one of which was designated 45-4/B-9.

45-4/B-9 was grown to confluency in a T-75 culture flask (DMEM+10% DFCS+700 μg/mL Geneticin) at 37° C., after which the cells were transferred to 27° C. and acclimatized for 3 days before an expression period of 24 hours. After the expression period, the FVIII:C concentration was measured to 12.8 U/mL using the chromogenic assay (Kabi).

Deposit Information

The following materials were deposited with the American Type Culture Collection:

| Plasmid | Deposit Date | Accession No. |
|---|---|---|
| pSVF8-92 | 24 January 1986 | 40222 |
| pSVF8-80 | 24 January 1986 | 40223 |
| pSVF8-200 | 17 July 1985 | 40190 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

Although the foregoing invention has been described in some detail by way of illustration and example for purposes of clarity of understanding, it will be obvious that certain changes and modifications may be practiced within the scope of the appended claims.

What is claimed:

1. A composition comprising Factor VIII:C proteins, wherein the Factor VIII:C proteins consist essentially of a first polypeptide comprising an amino acid sequence of the A domain of human Factor VIII:C as encoded by the polynucleotide present in plasmid pSVF8-200 (ATCC No. 40190) or an amino acid sequence that differs therefrom in having not more than 10 number % amino acid substitutions, and a second polypeptide comprising an amino acid sequence of the C domain of human Factor VIII:C as encoded by the polynucleotide present in plasmid pSVF8-200 (ATCC No. 40190) or an amino acid sequence that differs therefrom in having not more than 10 number % amino acid substitutions.

2. The composition of claim 1, comprising a complex of the first and second polypeptides.

3. The composition of claim 2, wherein the complex has human Factor VIII:C coagulant activity.

4. The composition of claim 1, comprising a $Ca^{++}$-bridged complex of the first and second polypeptides.

5. The composition of claim 4, wherein the complex has human Factor VIII:C coagulant activity.

6. The composition of claim 2, wherein the first polypeptide consists of the amino acid sequence of amino acids 1–740 of human Factor VIII:C as encoded by the polynucleotide present in plasmid pSVF8-200 (ATCC No. 40190), and the second polypeptide consists of the amino acid sequence of amino acids 1649–2332 of human Factor VIII:C as encoded by the polynucleotide present in plasmid pSVF8-200 (ATCC No. 40190).

7. The composition of claim 2, wherein the first polypeptide consists of amino acids 1–740 of human Factor VIII:C as encoded by the polynucleotide present in plasmid pSVF8-200 (ATCC No. 40190) or an amino acid sequence that differs therefrom in having not more than 10 number % amino acid substitutions, and the second polypeptide consists of amino acids 1649–2332 of human Factor VIII:C as encoded by the polynucleotide present in plasmid pSVF8-200 (ATCC No. 40190) or an amino acid sequence that differs therefrom in having not more than 10 number % amino acid substitutions.

8. The composition of claim 4, wherein the first polypeptide consists of the amino acid sequence of amino acids 1–740 of human Factor VIII:C as encoded by the polynucleotide present in plasmid pSVF8-200 (ATCC No. 40190), and the second polypeptide consists of the amino acid sequence of amino acids 1649–2332 of human Factor VIII:C as encoded by the polynucleotide present in plasmid pSVF8-200 (ATCC No. 40190).

9. The composition of claim 4, wherein the first polypeptide consists of amino acids 1–740 of human Factor VIII:C as encoded by the polynucleotide present in plasmid pSVF8-200 (ATCC No. 40190) or an amino acid sequence that differs therefrom in having not more than 10 number % amino acid substitutions, and the second polypeptide consists of amino acids 1649–2332 of human Factor VIII:C as encoded by the polynucleotide present in plasmid pSVF8-200 (ATCC No. 40190) or an amino acid sequence that differs therefrom in having not more than 10 number % amino acid substitutions.

10. The composition of claim 2, wherein the first polypeptide comprises the amino acid sequence of amino acid 1 of the A domain to an amino acid selected from the group consisting of amino acids 741–760 of the B domain as encoded by the polynucleotide present in plasmid pSVF8-200 (ATCC No. 40190) or an amino acid sequence that differs therefrom in having not more than 10 number % amino acid substitutions, and the second polypeptide comprises the amino acid sequence of amino acids 1649–2332 of human Factor VIII:C as encoded by the polynucleotide present in plasmid pSVF8-200 (ATCC No. 40190).

11. The composition of claim 4, wherein the first polypeptide comprises the amino acid sequence of amino acid 1 of the A domain to an amino acid selected from the group consisting of amino acids 741–760 of the B domain as encoded by the polynucleotide present in plasmid pSVF8-200 (ATCC No. 40190) or an amino acid sequence that differs therefrom in having not more than 10 number % amino acid substitutions, and the second polypeptide comprises the amino acid sequence of amino acids 1649–2332 of human Factor VIII:C as encoded by the polynucleotide present in plasmid pSVF8-200 (ATCC No. 40190).

12. The composition of claim 2, wherein the first polypeptide consists of the amino acid sequence of amino acids 1–1102 of human Factor VIII:C as encoded by the polynucleotide present in plasmid pSVF8-200 (ATCC No. 40190).

13. The composition of claim 2, wherein the first polypeptide consists of the amino acid sequence of amino acids 1–1315 of human Factor VIII:C as encoded by the polynucleotide present in plasmid pSVF8-200 (ATCC No. 40190).

14. The composition of claim 2, wherein the first polypeptide consists of the amino acid sequence of amino acids 1–1405 of human Factor VIII:C as encoded by the polynucleotide present in plasmid pSVF8-200 (ATCC No. 40190).

15. The composition of claim 2, wherein the first polypeptide consists of the amino acid sequence of amino acids 1–978 of human Factor VIII:C as encoded by the polynucleotide present in plasmid pSVF8-200 (ATCC No. 40190).

16. The composition of claim 2, wherein the first polypeptide consists of the amino acid sequence extending to an amino acid selected from the group consisting of amino acids 741–760 of human Factor VIII:C as encoded by the polynucleotide present in plasmid pSVF8-200 (ATCC No. 40190).

17. The composition of claim 4, wherein the first polypeptide consists of the amino acid sequence of amino acids 1–1102 of human Factor VIII:C as encoded by the polynucleotide present in plasmid pSVF8-200 (ATCC No. 40190).

18. The composition of claim 4, wherein the first polypeptide consists of the amino acid sequence of amino acids 1–1315 of human Factor VIII:C as encoded by the polynucleotide present in plasmid pSVF8-200 (ATCC No. 40190).

19. The composition of claim 4, wherein the first polypeptide consists of the amino acid sequence of amino acids 1–1405 of human Factor VIII:C as encoded by the polynucleotide present in plasmid pSVF8-200 (ATCC No. 40190).

20. The composition of claim 4, wherein the first polypeptide consists of the amino acid sequence of amino acids 1–978 of human Factor VIII:C as encoded by the polynucleotide present in plasmid pSVF8-200 (ATCC No. 40190).

21. The composition of claim 4, wherein the first polypeptide consists of the amino acid sequence extending to an amino acid selected from the group consisting of amino acids 741–760 of human Factor VIII:C as encoded by the polynucleotide present in plasmid pSVF8-200 (ATCC No. 40190).

22. The composition of claim 2, wherein not more than about 5 number % of the amino acids of the amino acid sequence of the first polypeptide are substituted.

23. The composition of claim 4, wherein not more than about 5 number % of the amino acids of the amino acid sequence of the first polypeptide are substituted.

24. The composition of claim 2, wherein the second polypeptide consists of the amino acid sequence from an amino acid selected from the group consisting of amino acids 1570–1649 to an amino acid selected from the group consisting of amino acids 2300–2332 of human Factor VIII:C as encoded by the polynucleotide present in plasmid pSVF8-200 (ATCC No. 40190).

25. The composition of claim 24, wherein the second polypeptide consists of the amino acid sequence from an amino acid selected from the group consisting of amino acids 1600–1649 to an amino acid selected from the group consisting of amino acids 2310–2332 of human Factor VIII:C as encoded by the polynucleotide present in plasmid pSVF8-200 (ATCC No. 40190).

26. The composition of claim 25, wherein the second polypeptide consists of the amino acid sequence from an amino acid selected from the group consisting of amino acids 1625–1649 to an amino acid selected from the group consisting of amino acids 2325–2332 of human Factor VIII:C as encoded by the polynucleotide present in plasmid pSVF8-200 (ATCC No. 40190).

27. The composition of claim 26, wherein the second polypeptide consists of the amino acid sequence from an amino acid selected from the group consisting of amino acids 1640–1649 to an amino acid selected from the group consisting of amino acids 2325–2332 of human Factor VIII:C as encoded by the polynucleotide present in plasmid pSVF8-200 (ATCC No. 40190).

28. The composition of claim 4, wherein the second polypeptide consists of the amino acid sequence from an amino acid selected from the group consisting of amino acids 1570–1649 to an amino acid selected from the group consisting of amino acids 2300–2332 of human Factor VIII:C as encoded by the polynucleotide present in plasmid pSVF8-200 (ATCC No. 40190).

29. The composition of claim 28, wherein the second polypeptide consists of the amino acid sequence from an amino acid selected from the group consisting of amino acids 1600–1649 to an amino acid selected from the group consisting of amino acids 2310–2332 of human Factor VIII:C as encoded by the polynucleotide present in plasmid pSVF8-200 (ATCC No. 40190).

30. The composition of claim 29, wherein the second polypeptide consists of the amino acid sequence from an amino acid selected from the group consisting of amino acids 1625–1649 to an amino acid selected from the group consisting of amino acids 2325–2332 of human Factor VIII:C as encoded by the polynucleotide present in plasmid pSVF8-200 (ATCC No. 40190).

31. The composition of claim 30, wherein the second polypeptide consists of the amino acid sequence from an amino acid selected from the group consisting of amino acids 1640–1649 to an amino acid selected from the group consisting of amino acids 2325–2332 of human Factor VIII:C as encoded by the polynucleotide present in plasmid pSVF8-200 (ATCC No. 40190).

32. A pharmaceutical composition comprising the composition of claim 1 and a physiologically acceptable carrier.

33. A pharmaceutical composition comprising the composition of claim 4 and a physiologically acceptable carrier.

34. A method for treating an individual requiring Factor VIII:C activity comprising administering to the individual a sufficient amount of the protein complex of claim 32 to enhance blood clotting activity in the individual.

35. A method for treating an individual requiring Factor VIII:C activity comprising administering to the individual a sufficient amount of the protein complex of claim 33 to enhance blood clotting activity in the individual.

* * * * *

```
                          SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: misc_difference
         (B) LOCATION: replace(1..4, "")
         (D) OTHER INFORMATION: /note= "Overhang:  not paired with
             complimentary strand."

(xi) SEQUENCE DESCRIPTION: SEQ ID NO:1:

AGCTAGATCT CCCGGGTCTA GATAAGTAAT                                     30

(2) INFORMATION FOR SEQ ID NO:2:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: misc_difference
         (B) LOCATION: replace(1..4, "")
         (D) OTHER INFORMATION: /note= "Overhang:  not paired with
             complimentary strand."

(xi) SEQUENCE DESCRIPTION: SEQ ID NO:2:

GATCATTACT TATCTAGACC CGGGAGATCT                                     30

(2) INFORMATION FOR SEQ ID NO:3:

(i) SEQUENCE CHARACTERISTICS:
         (A) LENGTH: 26 base pairs
```

```
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

AGATCTCGAA TTCCCCGGGG GTACCT                                          26

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
            complimentary strand."

(xi) SEQUENCE DESCRIPTION: SEQ ID NO:4:

CTAGAGGTAC CCCCGGGGAA TTCGAGATCT                                      30

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
            complimentary strand."

(xi) SEQUENCE DESCRIPTION: SEQ ID NO:5:

GATCTCGAAT TCCCCGGGTC TAGAGGATCC GTCGAC                               36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
            complimentary strand."

(xi) SEQUENCE DESCRIPTION: SEQ ID NO:6:

CTAGGTGCAC GGATCCTCTA GACCCGGGGA ATTCGA                               36

(2) INFORMATION FOR SEQ ID NO:7:

(i) SEQUENCE CHARACTERISTICS:
        (A) LENGTH: 49 base pairs
        (B) TYPE: nucleic acid
```

```
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
             complimentary strand."

(ix) FEATURE:
        (A) NAME/KEY: CDS
        (B) LOCATION: 36..47

(ix) FEATURE:
        (A) NAME/KEY: misc_difference
        (B) LOCATION: replace(46..49, "")
        (D) OTHER INFORMATION: /note= "Overhang:  not paired with
             complimentary strand."

(xi) SEQUENCE DESCRIPTION: SEQ ID NO:7:

GATCCTCTCC AGTTGAACAT TTGTAGCAAT AAGTC ATG CAA ATA GAG CT          49
                                      Met Gln Ile Glu
                                        1

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:8:

Met Gln Ile Glu
  1

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

CTATTTGCAT GACTTATTGC TACAAATGTT CAACTGGAGA G                      41

(2) INFORMATION FOR SEQ ID NO:10:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTCATGCAA                                                           9

(2) INFORMATION FOR SEQ ID NO:11:

(i) SEQUENCE CHARACTERISTICS:
        (A) LENGTH: 7 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:11:

ACCATGG                                                                            7

(2) INFORMATION FOR SEQ ID NO:12:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..135

(xi) SEQUENCE DESCRIPTION: SEQ ID NO:12:

ATG GAT GCA ATG AAG AGA GGG CTC TGC TGC TGT GTG CTG CTG TGT GGA          48
Met Asp Ala Met Lys Arg Gly Leu Cys Cys Cys Val Leu Leu Cys Gly
 1               5                  10                  15

GCA GTC TTC GTT TCG CCC AGC CAG GAA ATC CAT GCC CGA TTC AGA AGA          96
Ala Val Phe Val Ser Pro Ser Gln Glu Ile His Ala Arg Phe Arg Arg
                20                  25                  30

GGA GCC AGA TCT ATA ACT CGT ACT CTT CAG CAG TCT GAT                     135
Gly Ala Arg Ser Ile Thr Arg Thr Leu Gln Gln Ser Asp
            35                  40                  45

(2) INFORMATION FOR SEQ ID NO:13:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:13:

Met Asp Ala Met Lys Arg Gly Leu Cys Cys Cys Val Leu Leu Cys Gly
 1               5                  10                  15

Ala Val Phe Val Ser Pro Ser Gln Glu Ile His Ala Arg Phe Arg Arg
                20                  25                  30

Gly Ala Arg Ser Ile Thr Arg Thr Leu Gln Gln Ser Asp
            35                  40                  45

(2) INFORMATION FOR SEQ ID NO:14:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..135

(xi) SEQUENCE DESCRIPTION: SEQ ID NO:14:

ATG GAT GCA ATG AAG AGA GGG CTC TGC TGC TGT GTG CTG CTG TGT GGA          48
Met Asp Ala Met Lys Arg Gly Leu Cys Cys Cys Val Leu Leu Cys Gly
 1               5                  10                  15

```
GCA GTC TTC GTT TCG CCC AGC CAG GAA ATC CAT GCC CGA TTC AGA AGA        96
Ala Val Phe Val Ser Pro Ser Gln Glu Ile His Ala Arg Phe Arg Arg
            20                  25                  30

GGA GCC AGA GAA ATA ACT CGT ACT CTT CAG CAG TCT GAT                   135
Gly Ala Arg Glu Ile Thr Arg Thr Leu Gln Gln Ser Asp
        35                  40                  45
```

(2) INFORMATION FOR SEQ ID NO:15:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asp Ala Met Lys Arg Gly Leu Cys Cys Cys Val Leu Leu Cys Gly
 1               5                  10                  15

Ala Val Phe Val Ser Pro Ser Gln Glu Ile His Ala Arg Phe Arg Arg
            20                  25                  30

Gly Ala Arg Glu Ile Thr Arg Thr Leu Gln Gln Ser Asp
        35                  40                  45
```

(2) INFORMATION FOR SEQ ID NO:16:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..126

(xi) SEQUENCE DESCRIPTION: SEQ ID NO:16:

```
ATG GAT GCA ATG AAG AGA GGG CTC TGC TGC TGT GTG CTG CTG TGT GGA        48
Met Asp Ala Met Lys Arg Gly Leu Cys Cys Cys Val Leu Leu Cys Gly
 1               5                  10                  15

GCA GTC TTC GTT TCG CCC AGC GAG ATA ACT CGT ACT CTT CAG CAG TCT        96
Ala Val Phe Val Ser Pro Ser Glu Ile Thr Arg Thr Leu Gln Gln Ser
            20                  25                  30

GAT CAA GAG GAA ATT GAC TAT GAT GAT ACC                               126
Asp Gln Glu Glu Ile Asp Tyr Asp Asp Thr
        35                  40
```

(2) INFORMATION FOR SEQ ID NO:17:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asp Ala Met Lys Arg Gly Leu Cys Cys Cys Val Leu Leu Cys Gly
 1               5                  10                  15

Ala Val Phe Val Ser Pro Ser Glu Ile Thr Arg Thr Leu Gln Gln Ser
            20                  25                  30

Asp Gln Glu Glu Ile Asp Tyr Asp Asp Thr
        35                  40
```

(2) INFORMATION FOR SEQ ID NO:18:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..126

(xi) SEQUENCE DESCRIPTION: SEQ ID NO:18:

```
ATG GAT GCA ATG AAG AGA GGG CTC TGC TGC TGT GTG CTG CTG TGT GGA      48
Met Asp Ala Met Lys Arg Gly Leu Cys Cys Cys Val Leu Leu Cys Gly
 1               5                  10                  15

GCA GTC TTC GTT TCG CCC AGC CAG GAA ATC CAT GCC CGA TTC AGA AGA      96
Ala Val Phe Val Ser Pro Ser Gln Glu Ile His Ala Arg Phe Arg Arg
             20                  25                  30

GAG ATA ACT CGT ACT CTT CAG CAG TCT GAT                             126
Glu Ile Thr Arg Thr Leu Gln Gln Ser Asp
         35                  40
```

(2) INFORMATION FOR SEQ ID NO:19:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:19:

```
Met Asp Ala Met Lys Arg Gly Leu Cys Cys Cys Val Leu Leu Cys Gly
 1               5                  10                  15

Ala Val Phe Val Ser Pro Ser Gln Glu Ile His Ala Arg Phe Arg Arg
             20                  25                  30

Glu Ile Thr Arg Thr Leu Gln Gln Ser Asp
         35                  40
```

(2) INFORMATION FOR SEQ ID NO:20:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..126

(xi) SEQUENCE DESCRIPTION: SEQ ID NO:20:

```
ATG GAT GCA ATG AAG AGA GGG CTC TGC TGC TGT GTG CTG CTG TGT GGA      48
Met Asp Ala Met Lys Arg Gly Leu Cys Cys Cys Val Leu Leu Cys Gly
 1               5                  10                  15

GCA GTC TTC GTT TCG CCC AGC CAG GAA ATC CAT GCC GAG ATA ACT CGT      96
Ala Val Phe Val Ser Pro Ser Gln Glu Ile His Ala Glu Ile Thr Arg
             20                  25                  30

ACT CTT CAG CAG TCT GAT CAA GAG GAA ATT                             126
Thr Leu Gln Gln Ser Asp Gln Glu Glu Ile
         35                  40
```

(2) INFORMATION FOR SEQ ID NO:21:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:21:

```
Met Asp Ala Met Lys Arg Gly Leu Cys Cys Val Leu Leu Cys Gly
 1               5                  10                  15

Ala Val Phe Val Ser Pro Ser Gln Glu Ile His Ala Glu Ile Thr Arg
                20                  25                  30

Thr Leu Gln Gln Ser Asp Gln Glu Glu Ile
                35                  40
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Xaa Ile Xaa Arg Thr Xaa Leu Gln Xaa Asp Gln
 1               5                  10
```

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Xaa Xaa Arg Glu Ile Thr Arg Thr Thr Leu
 1               5                  10
```

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Ser Glu Ile Thr Arg Thr
 1               5
```

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Xaa Gln Glu Ile
1

(2) INFORMATION FOR SEQ ID NO:26:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..135

(xi) SEQUENCE DESCRIPTION: SEQ ID NO:26:

```
ATG CCC TCG AGC GTC TCG TGG GGC ATC CTC CTG CTG GCA GGC CTG TGC        48
Met Pro Ser Ser Val Ser Trp Gly Ile Leu Leu Leu Ala Gly Leu Cys
 1               5                  10                  15

TGC CTG GTC CCT GTC TCC CTG GCT GAG ATC ACT CGT ACT ACT CTT CAG        96
Cys Leu Val Pro Val Ser Leu Ala Glu Ile Thr Arg Thr Thr Leu Gln
                20                  25                  30

TCT GAT CAA GAG GAA ATT GAC TAT GAT GAT ACC ATA TCA                   135
Ser Asp Gln Glu Glu Ile Asp Tyr Asp Asp Thr Ile Ser
            35                  40                  45
```

(2) INFORMATION FOR SEQ ID NO:27:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:27:

```
Met Pro Ser Ser Val Ser Trp Gly Ile Leu Leu Leu Ala Gly Leu Cys
 1               5                  10                  15

Cys Leu Val Pro Val Ser Leu Ala Glu Ile Thr Arg Thr Thr Leu Gln
                20                  25                  30

Ser Asp Gln Glu Glu Ile Asp Tyr Asp Asp Thr Ile Ser
            35                  40                  45
```

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Glu Ile Thr Arg Thr Xaa Leu Gln Ser Asp Gln
1               5                  10

(2) INFORMATION FOR SEQ ID NO:29:

(i) SEQUENCE CHARACTERISTICS:
        (A) LENGTH: 109 base pairs
        (B) TYPE: nucleic acid
        (C) STRANDEDNESS: double (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
            complimentary strand."

(ix) FEATURE:
        (A) NAME/KEY: CDS
        (B) LOCATION: 1..102

(xi) SEQUENCE DESCRIPTION: SEQ ID NO:29:

```
AGC TTC TCC CAG AAT TCT AGA CAC CCT AGC ACT AGG CAA AAG CAA TTT        48
Ser Phe Ser Gln Asn Ser Arg His Pro Ser Thr Arg Gln Lys Gln Phe
 1               5                  10                  15

AAT GCC ACC CCT CCT ACA CCA CCA ACC CCA CCA GTA CTG AAA CGC CAT        96
Asn Ala Thr Pro Pro Thr Pro Pro Thr Pro Pro Val Leu Lys Arg His
                20                  25                  30

CAA CGG TGATAAG                                                       109
Gln Arg
```

(2) INFORMATION FOR SEQ ID NO:30:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:30:

```
Ser Phe Ser Gln Asn Ser Arg His Pro Ser Thr Arg Gln Lys Gln Phe
 1               5                  10                  15

Asn Ala Thr Pro Pro Thr Pro Pro Thr Pro Pro Val Leu Lys Arg His
                20                  25                  30

Gln Arg
```

(2) INFORMATION FOR SEQ ID NO:31:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(1..4, "")
        (D) OTHER INFORMATION: /note= "Overhang:  not paired with
            complimentary strand."

(xi) SEQUENCE DESCRIPTION: SEQ ID NO:31:

```
TCGACTTATC ACCGTTGATG GCGTTTCAGT ACTGGTGGGG TTGGTGGTGT AGGAGGGGTG         60

GCATTAAATT GCTTTTGCCT AGTGCTAGGG TGTCTAGAAT CTGGGAGA                    109
```